US009101578B2

(12) United States Patent
Galarza et al.

(10) Patent No.: US 9,101,578 B2
(45) Date of Patent: Aug. 11, 2015

(54) POLYVALENT INFLUENZA VIRUS-LIKE PARTICLE (VLP) COMPOSITIONS

(75) Inventors: Jose M. Galarza, Scarsdale, NY (US); Demetrius Matassov, Richmond Hill, NY (US)

(73) Assignee: TechnoVax, Inc., Tarrytown, NY (US)

( * ) Notice: Subject to any disclaimer, the term of this patent is extended or adjusted under 35 U.S.C. 154(b) by 1741 days.

(21) Appl. No.: 11/796,987

(22) Filed: Apr. 30, 2007

(65) Prior Publication Data

US 2009/0022762 A1  Jan. 22, 2009

Related U.S. Application Data

(60) Provisional application No. 60/796,738, filed on May 1, 2006.

(51) Int. Cl.
| A61K 39/145 | (2006.01) |
| C07K 14/005 | (2006.01) |
| A61K 39/12 | (2006.01) |
| A61K 39/00 | (2006.01) |

(52) U.S. Cl.
CPC ............... *A61K 39/145* (2013.01); *A61K 39/12* (2013.01); *C07K 14/005* (2013.01); *A61K 2039/5258* (2013.01); *A61K 2039/70* (2013.01); *C12N 2760/16122* (2013.01); *C12N 2760/16123* (2013.01); *C12N 2760/16134* (2013.01); *C12N 2760/16222* (2013.01); *C12N 2760/16223* (2013.01); *C12N 2760/16234* (2013.01)

(58) Field of Classification Search
CPC ..................... A61K 2039/5258; A61K 39/145; A61K 39/12; A61K 2039/543; A61K 2039/5256; A61K 2039/70; A61K 2039/6075; C07K 14/005; C07K 2319/00; C07K 16/1018; C07K 2317/33; C07K 2319/735; C07K 14/11; C07K 1/00; C12N 2760/16134; C12N 2760/16123; C12N 2760/16122; C12N 2760/16223; C12N 2760/18523; C12N 2760/16234; C12N 2760/16022; C12N 2760/16222; C12N 2760/16051; C12N 2760/16323; C12N 2760/16111; C12N 2760/16211

See application file for complete search history.

(56) References Cited

U.S. PATENT DOCUMENTS

| 7,226,774 | B2 | 6/2007 | Kawaoka | |
| 2003/0035814 | A1* | 2/2003 | Kawaoka et al. | .......... 424/208.1 |
| 2003/0194694 | A1* | 10/2003 | Kawaoka | .......................... 435/5 |
| 2005/0009008 | A1 | 1/2005 | Robinson et al. | |
| 2005/0186621 | A1 | 8/2005 | Galarza et al. | |
| 2006/0263804 | A1 | 11/2006 | Robinson et al. | |
| 2007/0184526 | A1 | 8/2007 | Smith et al. | |
| 2008/0003239 | A1* | 1/2008 | Duke et al. | ................. 424/206.1 |

FOREIGN PATENT DOCUMENTS

| WO | WO 2005/020889 A2 | 3/2005 |
| WO | WO 2006/135413 A2 | 12/2006 |
| WO | WO 2007/047831 A2 | 4/2007 |

OTHER PUBLICATIONS

Hui et al., YRKL Sequence of Influenza Virus M1 Functions as the L Domain Motif and Interacts with VPS28 and Cdc42, 2006, Journal of Virology, vol. 80, No. 5, pp. 2291-2308.*
Faulkner et al., Influenza hemagglutinin peptides fused to interferon gamma and encapsulated in liposomes protects mice against influenza infection, 2003, Vaccine, vol. 21, pp. 932-939.*
Hui et al., Basic Residues of the Helix Six Domain of Influenza Virus M1 Involved in Nuclear Translocation of M1 Can Be Replaced by PTAP and YPDL Late Assembly Domain Motifs, 2003, Journal of Virology, vol. 77, No. 12, pp. 7078-7092.*
Wanatabe et al., Mechanism for Inhibition of Influenza Virus RNA Polymerase Activity by Matrix Protein, 1996, Journal of Virology, vol. 70, No. 1, pp. 241-247.*
Elleman and Barclay, The M1 matrix protein controls the filamentous phenotype of influenza A virus, 2004, Virology, vol. 321, pp. 144-153.*
Burleigh et al., Influenza A Viruses with Mutations in the M1 Helix Six Domain Display a Wide Variety of Morphological Phenotypes, 2005, Journal of Virology, vol. 79, No. 2, pp. 1262-1270.*
Watanabe, et al., "Immunogenicity and Protective Efficacy of Replication-Incompetent Influenza Virus-Like Particles," *Journal of Virology* 76:767-773 (2002).
Baker, et al., "Structure of Bovine and Human Papillomaviruses: Analysis by Cryoelectron Microscopy and Three-Dimensional Image Reconstruction," *Biophys J* 60:1445-1456 (1991).
Caton, et al., The Antigenic Structure of the Influenza Virus A/PR/8/34 Hemaglutinin (H1 Subtype) *Cell* 31:417-427 (1982).
Galarza, et al., "Virus-Like Particle (VLP) Vaccine Conferred Complete Protection Against a Lethal Influenza Virus Challenge," *Viral Immunol* 18(1):244-251 (2005).
Galarza, et al., "Virus-Like Particle (VLP) Vaccine Conferred Complete Protection Against a Lethal Influenza Virus Challenge," *Viral Immunol* 18(2):365-372 (2005).
Gerhard, et al., "Antigenic Structure of Influenza Virus Haemagglutinin Defined by Hybridoma Antibodies," *Nature* 290:713-717(1981).
Glaser, et al., "A Single Amino Acid Substitutuin in 1918 Inluenza Virus Hemagglutinin Changes Recepto Binding Specificity," *J Virol* 79(17):11533-11536 (2005).
Gomez-Puertas, et al., "Influenza Virus is the Major Driving Force in Virus Budding," *J Virol* 74(24):11538-11547 (2000).
Hagensee, et al., "Three-Dimensional Structure of Vaccinia Virus-Produced Human Papillomavirus Type 1 Capsids," *J Viral* 68(7):4503-4505 (1994).

(Continued)

*Primary Examiner* — Benjamin P Blumel
(74) *Attorney, Agent, or Firm* — Pasternak Patent Law; Dahna S. Pasternak

(57) ABSTRACT

Polyvalent influenza virus-like particles (VLPs) comprising influenza antigenic polypeptides are described. Also described are compositions comprising these polyvalent VLPs as well as methods of making and using these VLPs.

20 Claims, 12 Drawing Sheets

(56) References Cited

OTHER PUBLICATIONS

Iwatsuki-Horimoto, et al., "The Index Influenza A Virus Subtype H5N1 Isolated from a Human in 1997 Differs in its Receptor-Binding Properties from a Virulent Avian Influenza Virus," *J General Virol* 85:1001-1005 (2004).

Knossow, et al., "Variation and Infectivity Neutralization in Influenza," *Immunology* 119:1-7 (2006).

Latham, et al., "Formation of Wild-Type and Chimeric Influenza Virus-Like Particles Following Simultaneous Expression of Only Four Structural Proteins," *J Virol* 75(13):6154-6165 (2001).

Pushko, et al, "Influenza Virus-Like Particles Comprised of the HA, NA, and M1 Proteins of H9N2 Influenza Virus Induced Protective Immune Responses in BALB/c Mice," *Vaccine* 23:5751-5759 (2005).

Stephenson, et al., "Detection of Anti-H5 Responses in Human Sera by HI Using Horse Erythrocytes Following MF59-Adjuvented Influenza A/Duck/Singapore/97 Vaccine," *Virus Res* 103:91-95 (2004).

Thomas, et al., "Avian Influenza: A Review," *Am J Health-Syst Pharm* 64:149-165 (2007).

"Epidemiology of WHO-Confirmed Human Cases of Avian Influenza A9H5N1) Infection," World Health Organization, Geneva, *Weekly Epidemiological Record* 81(26):249-260 (2006).

\* cited by examiner

```
    ATGAATCCAAATCAAAAGATAATAAACAATTGGCTCTGTCTCTCTCACCATTGCAACAATATGCTTCCTCATGCAGATTGC
1   --------+---------+---------+---------+---------+---------+---------+---------+ 80
    TACTTAGGTTTAGTTTTCTATTATTGTTAACCGAGACAGAGAGAGTGGTAACGTTGTTATACGAAGGAGTACGTCTAACG
    M  N  P  N  Q  K  I  I  T  I  G  S  V  S  L  T  I  A  T  I  C  F  L  M  Q  I  A

CATCCTGGTAACTACTGTAACATTG                                  (Seq ID No: 2)
81  --------+---------+----- 105
    GTAGGACCATTGATGACATTGTAAC                                  (Seq ID No: 3)
    I  L  V  T  T  V  T  L                                     (Seq ID No: 4)
```

Fig. 12

```
    TACAAAGACTGGATCCTGTGGATTTCCTTTGCCATATCATGCTTTTTGCTTTGTGTTGTTTTGCTCGGGTTCATCATGTGGGCCTGCCAGAAAGGCAACA
1   --------+---------+---------+---------+---------+---------+---------+---------+---------+---------+ 100
    ATGTTTCTGACCTAGGACACCTAAAGGAAACGGTATAGTAGTACGAAAAACGACCCAAGTAGTACACCCGGACGTCTTTCCGTTGT
    Y  K  D  W  I  L  W  I  S  F  A  I  S  C  F  L  C  V  V  L  L  G  F  I  M  W  A  C  Q  K  G  N  I

TTAGGTGCAACATTTGCATT               (Seq ID No: 5)
101 --------+---------+ 120
    AATCCACGTTGTAAACGTAA               (Seq ID No: 6)
    R  C  N  I  C  I                   (Seq ID No: 7)
``` atgaatccaaatcagaaaataataaccattggatcaatctgtctggtagtcgga (Seq ID No: 8)
M  N  P  N  Q  K  I  I  T  I  G  S  I  C  L  V  V  G   (Seq ID No: 9)

Ctaattagcctaatattgcaaataggaatataatctcaatatggattagc
L  I  S  L  I  L  Q  I  G  N  I  I  S  I  W  I  S

Fig. 13 gattctggcgatctactcaactgtcgccagttcactgtgcttttggtctccctgggggcaatc  (Seq ID No: 10)
I  L  A  I  Y  S  T  V  A  S  S  L  V  L  L  V  S  L  G  A  I    (Seq ID No: 11)

Agtttctggatgtgttctaatggatctttgcagtgcagaatatgcatc
S  F  W  M  C  S  N  G  S  L  Q  C  R  I  C  I

Fig. 14

```
                           SEQUENCE LISTING

<160> NUMBER OF SEQ ID NOS: 11

<210> SEQ ID NO 1
<211> LENGTH: 5
<212> TYPE: PRT
<213> ORGANISM: Influenza Virus A/PR/8/34 H1N1

<400> SEQUENCE: 1

Arg Lys Leu Lys Arg
1               5

<210> SEQ ID NO 2
<211> LENGTH: 105
<212> TYPE: DNA
<213> ORGANISM: Influenza Virus A/Udorn/72 H3N2

<400> SEQUENCE: 2
atgaatccaa atcaaaagat aataacaatt ggctctgtct ctctcaccat tgcaacaata      60
tgcttcctca tgcagattgc catcctggta actactgtaa cattg                    105

<210> SEQ ID NO 3
<211> LENGTH: 105
<212> TYPE: DNA
<213> ORGANISM: Influenza Virus A/Udorn/72 H3N2

<400> SEQUENCE: 3
tacttaggtt tagttttcta ttattgttaa ccgagacaga gagagtggta acgttgttat      60
acgaaggagt acgtctaacg gtaggaccat tgatgacatt gtaac                    105

<210> SEQ ID NO 4
<211> LENGTH: 35
<212> TYPE: PRT
<213> ORGANISM: Influenza Virus A/Udorn/72 H3N2

<400> SEQUENCE: 4

Met Asn Pro Asn Gln Lys Ile Ile Thr Ile Gly Ser Val Ser Leu Thr
1               5                  10                  15

Ile Ala Thr Ile Cys Phe Leu Met Gln Ile Ala Ile Leu Val Thr Thr
            20                  25                  30

Val Thr Leu
        35
```

<210> SEQ ID NO 5
<211> LENGTH: 120
<212> TYPE: DNA
<213> ORGANISM: Influenza Virus A/Udorn/72 H3N2

<400> SEQUENCE: 5
tacaaagact ggatcctgtg gatttccttt gccatatcat gcttttgct ttgtgttgtt      60 ttgctggggt tcatcatgtg ggcctgccag aaaggcaaca ttaggtgcaa catttgcatt    120

<210> SEQ ID NO 6
<211> LENGTH: 120
<212> TYPE: DNA
<213> ORGANISM: Influenza Virus A/Udorn/72 H3N2

<400> SEQUENCE: 6
atgtttctga cctaggacac ctaaaggaaa cggtatagta cgaaaaacga acacaacaa      60 aacgacccca gtagtacac ccggacggtc tttccgttgt aatccacgtt gtaaacgtaa     120

<210> SEQ ID NO 7
<211> LENGTH: 40
<212> TYPE: PRT
<213> ORGANISM: Influenza Virus A/Udorn/72 H3N2

<400> SEQUENCE: 7

Tyr Lys Asp Trp Ile Leu Trp Ile Ser Phe Ala Ile Ser Cys Phe Leu
1               5                   10                  15

Leu Cys Val Val Leu Leu Gly Phe Ile Met Trp Ala Cys Gln Lys Gly
            20                  25                  30

Asn Ile Arg Cys Asn Ile Cys Ile
        35                  40

<210> SEQ ID NO 8
<211> LENGTH: 105
<212> TYPE: DNA
<213> ORGANISM: Influenza Virus A/PR/8/34 H1N1

<400> SEQUENCE: 8
atgaatccaa atcagaaaat aataaccatt ggatcaatct gtctggtagt cggactaatt      60
agcctaatat tgcaaatagg gaatataatc tcaatatgga ttagc                    105

<210> SEQ ID NO 9
<211> LENGTH: 35
<212> TYPE: PRT
<213> ORGANISM: Influenza Virus A/PR/8/34 H1N1

<400> SEQUENCE: 9

Met Asn Pro Asn Gln Lys Ile Ile Thr Ile Gly Ser Ile Cys Leu Val
1               5                   10                  15

Val Gly Leu Ile Ser Leu Ile Leu Gln Ile Gly Asn Ile Ile Ser Ile
            20                  25                  30

Trp Ile Ser
        35

<210> SEQ ID NO 10
<211> LENGTH: 112
<212> TYPE: DNA
<213> ORGANISM: Influenza Virus A/PR/8/34 H1N1

<400> SEQUENCE: 10
gattctggcg atctactcaa ctgtcgccag ttcactggtg cttttggtct ccctggggggc     60

-continued

```
aatcagtttc tggatgtgtt ctaatggatc tttgcagtgc agaatatgca tc        112
```

<210> SEQ ID NO 11
<211> LENGTH: 37
<212> TYPE: PRT
<213> ORGANISM: Influenza Virus A/PR/8/34 H1N1

<400> SEQUENCE: 11

```
Ile Leu Ala Ile Tyr Ser Thr Val Ala Ser Ser Leu Val Leu Leu Val
1               5                   10                  15

Ser Leu Gly Ala Ile Ser Phe Trp Met Cys Ser Asn Gly Ser Leu Gln
            20                  25                  30

Cys Arg Ile Cys Ile
            35
```

POLYVALENT INFLUENZA VIRUS-LIKE PARTICLE (VLP) COMPOSITIONS

CROSS REFERENCE TO RELATED APPLICATIONS

This application claims priority from U.S. Provisional Application No. 60/796,738, filed May 1, 2006. The entire disclosure of the above-referenced application is incorporated herein by reference.

STATEMENT AS TO FEDERALLY SPONSORED RESEARCH

Funds used to support some of the studies disclosed herein were provided by grant number 1 R43 AI063830-01 awarded by the National Institute of Allergy and Infectious Disease (NIAID) of the National Institutes of Health (NIH). The U.S. Government may have certain rights in the invention.

TECHNICAL FIELD

Multivalent virus-like particles (VLPs) containing influenza antigens are described, as are methods and making and using these VLPs.

BACKGROUND

The influenza A virus is a well characterized virus that infects humans as well as a large number of other species. See, e.g., U.S. Patent Publication No. 20050186621. All of the sixteen (Knossow M and Skehel J. J. (2006) *Immunology* 119(1):1-7) subtypes of influenza A virus circulate in wild birds and domestic avian species. Few influenza subtypes are epidemic among humans, but periodically pandemic strains derived from animals or birds unpredictably emerge causing wide spread disease of high morbidity and mortality.

Currently, influenza vaccines are produced in fertilized chicken eggs. Eleven days after fertilization, a single strain of influenza virus is injected into the eggs. The virus multiplies in the infected embryo and after several days of incubation, the eggs are opened the virus harvested, purified, chemically inactivated for killed vaccine) and combined with other similarly produced strains to generate an influenza vaccine. On average, one to two eggs are needed to produce one dose of vaccine and the entire production process lasts at least six months.

Traditional influenza vaccines are trivalent in that they contain antigenic proteins from three, different influenza virus strains (e.g., two subtypes A and one subtype B). Accordingly, each antigenically distinct virus must be produced separately in embryonated eggs or tissue culture, isolated and then combined in the final vaccine formulation meaning that one hundred million doses of vaccine necessitate the use of one hundred million eggs to produce only one of the vaccine components. The production of the three virus components currently included in the vaccine requires the use of three hundred million eggs or has similar production requirements in a tissue culture production process. Given the long and costly production protocols, it is unlikely that egg-based production of flu vaccines could be used to contain a flu pandemic.

Therefore, there remains a need for polyvalent influenza compositions and methods that prevent and/or treat infection with the various highly virulent and transmissible influenza strains.

SUMMARY

Described herein are polyvalent virus-like particles (VLPs) comprising two or more influenza proteins (e.g., antigens, structural proteins), preferably two or more antigenic influenza polypeptides from different strains. Also described are compositions comprising these VLPs, as well as methods for making and using these VLPs. The polyvalent VLPs preferably comprise influenza matrix protein M1 and at least two HA antigens derived from different influenza virus strains and/or at least two NA antigens derived from different influenza virus strains. Methods of making and using these compositions are also described.

VLP are structures that morphologically resemble an influenza virus, but are devoid of the genetic material required for viral replication and infection. Using VLPs rather than inactivated influenza virus for the production of polyvalent VLP vaccines has several advantages, including ease of production and purification, as compared current vaccines which are manufactured in eggs. Influenza VLP vaccine compositions may also avoid or reduce the unwanted side effects of current inactivated, egg-based vaccines seen in young children, elderly, and people with allergies to components of eggs. Furthermore, unlike many inactivated influenza virus vaccines, the HA and NA proteins of the VLPs described herein maintain conformational epitopes involved in eliciting a protective neutralizing antibody response. Using polyvalent VLPs presenting HA and/or NA proteins from multiple influenza strains allows immune responses to be generated to one or more influenza strains, reduces vaccine production costs, and allows vaccines to be safely produced to highly pathogenic viruses. Thus, the polyvalent VLPs described herein provides for enhanced vaccine safety, coverage, efficacy and ease in manufacturing and allows for the safe creation of polyvalent vaccines against multiple human and avian influenza viruses.

In one aspect, provided herein is a polyvalent influenza VLP comprising at least one influenza matrix protein (M1 and optionally M2) and two or more antigenic influenza glycoproteins, wherein the antigenic glycoproteins are derived from two or more different influenza strains. In certain embodiments, the VLP includes a single matrix protein, for example M1. In other embodiments, the VLP comprises M1 and M2. In certain embodiments, the glycoproteins are selected from the group consisting of HA, NA and combinations thereof.

Any of the VLPs described herein may further comprise an influenza nucleoprotein (NP) and/or one or two proteins of the polymerase complex (made up of PB1, PB2 and PA). For example, the VLP may include NP and/or PB1, PB2 and PA; NP and/or PB1 and PB2; NP and/or PB1 and PA; and/or NP and/or PB2 and PA.

In any of the polyvalent VLPs described herein, the M1 protein may comprise an amino acid modification as compared to a wild-type M1 protein, for example, modifications to one or more of the following: modification of the nuclear localization signal (NLS); modification of one or more determinants of spherical structure; modification of one or more amino acid residues involved in protein-protein interactions; and/or introduction of one or more L-domains.

In any of the VLPs described herein, the M1 and/or optional M2 protein may comprise an amino acid modification as compared to a wild-type matrix protein, for example, introduction of one or more L-domains and/or creation of a fusion of the matrix protein and an immunomodulatory polypeptide.

In yet another aspect, the disclosure provides a polyvalent VLP in which a portion of one or more of the glycoproteins proteins of any of the VLPs described herein is replaced with a homologous region of a glycoprotein protein from a different influenza strain or subtype. In certain embodiments, the transmembrane domain of the glycoprotein is replaced. In other embodiments, the cytoplasmic tail region of the glycoprotein is replaced. In yet other embodiments, the transmembrane domain and the cytoplasmic tail region of one or more glycoproteins are replaced with domains from one or more different influenza proteins.

In another aspect, described herein is a host cell comprising any of the VLPs as described above. The host cell may be an insect, plant, mammalian, bacterial or fungal cell.

In yet another aspect, a cell stably transfected with a sequence encoding an influenza matrix protein or an influenza glycoprotein is provided. The cell may be an insect, plant, mammalian, bacterial or fungal cell. In certain embodiments, the cell is a mammalian cell line.

In another aspect, a packaging cell line is provided for producing influenza VLPs as described herein. The cell line is stably transfected with one or more polynucleotides encoding less than all of the M1, HA and NA of the VLP (e.g., at least one of the influenza proteins forming the VLP), and upon introduction and expression of the one or more influenza protein-encoding sequences not stably transfected into the cell, the VLP is produced by the cell. In certain embodiments, sequences encoding M1 and/or M2 are stably integrated into the packaging cell line and sequences encoding the glycoproteins expressed on the surface of the VLP are introduced into the cell such that the VLP is formed. In other embodiments, sequences encoding one or more of the glycoproteins are stably integrated into the cell to form a packaging cell line and VLPs are formed upon introduction of sequences encoding M1 and, optionally, M2. The packaging cell may be an insect, plant, mammalian, bacterial or fungal cell. In certain embodiments, the packaging cell is a mammalian cell line.

In yet another aspect, the disclosure provides an immunogenic composition comprising any of the VLPs described herein and a pharmaceutically acceptable excipient. In certain embodiments, the compositions further comprise one or more adjuvants.

In a still further aspect, a method of producing a VLP as described herein is provided, the method comprising the steps of: expressing one or more polynucleotides encoding the M1 and at least two influenza glycoproteins in a suitable host cell under conditions such that the VLPs assemble in the host cell; and isolating the assembled VLPs from the host cell. The host cell can be a mammalian cell, an insect cell, a yeast cell or a fungal cell. In certain embodiments, an expression vector comprising one or more polynucleotides operably linked to control elements compatible with expression in the selected host cell are introduced into the host cell. The expression vector may be a plasmid, a viral vector, a baculovirus vector or a non-viral vector. In certain embodiments, one or more of the polynucleotides are stably integrated into the host cell. Alternatively, one or more of the polynucleotides may be transiently introduced into the host cell.

In another aspect, provided herein is a method of generating an immune response in a subject to two or more influenza viruses, the method comprising the step of administering a composition comprising one or more polyvalent VLPs as described herein to the subject. In certain embodiments, the composition is administered intranasally. Any of the methods may involve multiple administrations (e.g., a multiple dose schedule).

BRIEF DESCRIPTION OF THE DRAWINGS

Figure 1:
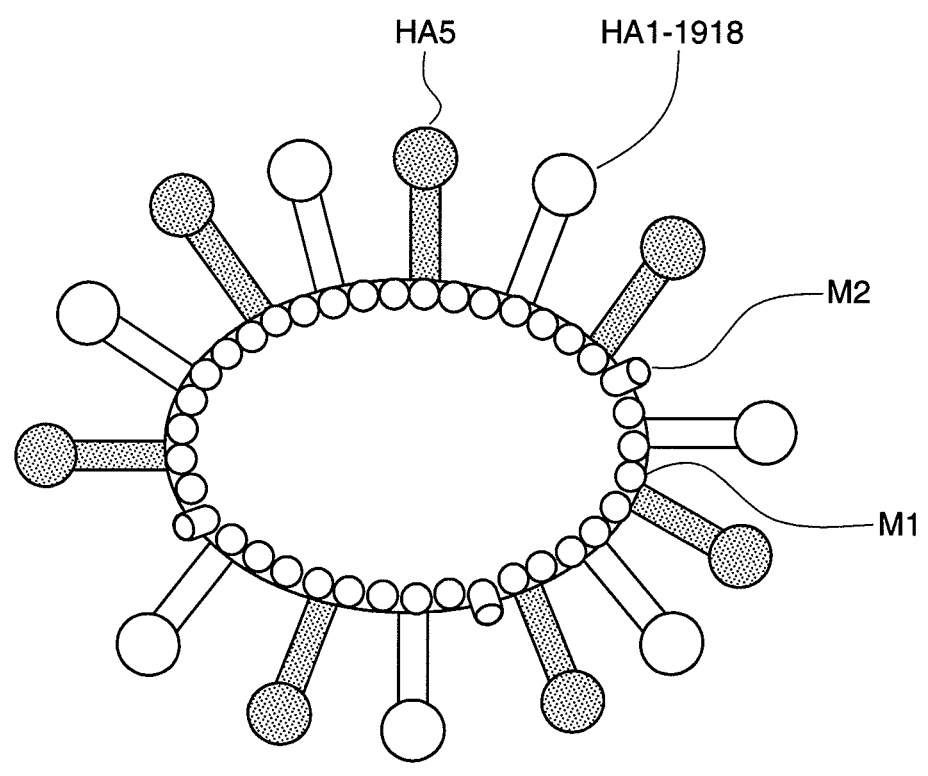

FIG. 1 is a schematic depicting the structure of exemplary polyvalent sub-viral structures (VLPs) as described herein. The matrix M1 protein underlines the membrane of the structure and the M2 protein forms a channel across the sub-viral structural membrane. The surface of the VLP is decorated with multiple antigenically distinct glycoproteins.

FIG. 6, panels A and B, depict Western blot analysis of polyvalent VLPs prepared as described in Example 1.

FIG. 7, panels A and B, depict electron micrographs of exemplary polyvalent VLPs.

FIG. 11 depicts the nucleotide (SEQ ID NOs:2 and 3) and amino acid sequence (SEQ ID NO:4) of amino terminus of A/Udorn/72 (H3N2) Neuraminidase (NA) protein, including the cytoplasmic tail and transmembrane domains. The NA cytoplasmic tail contains six N-terminal residues (MNP-NQK, shown in bold) which are identical sequence almost all nine known NA subtypes. The transmembrane domain is underlined.

FIG. 12 depicts the (SEQ ID NOs:5 and 6) and amino acid sequence (SEQ ID NO:7) of amino terminus of A/Udorn/72 hemagglutinin (HA) protein, including the cytoplasmic tail and transmembrane domains. The HA cytoplasmic tail contains 10-12 residues (QKGNIRCNICI, shown in bold) which are highly conserved between influenza strains. The transmembrane domain is underlined and three residues of the ectodomain (YKD) are shown in lower case.

FIG. 13 depicts the nucleotide (SEQ ID NO:8) and amino acid sequence (SEQ ID NO:9) of amino terminus of influenza A/PR/8/34 (H1N1) Neuraminidase (NA) protein, including the cytoplasmic tail and transmembrane domains. The NA cytoplasmic tail contains six N-terminal residues (MNP- NQK, shown in bold) which are identical sequence almost all nine known NA subtypes. The transmembrane domain is underlined.

FIG. 14 depicts the nucleotide (SEQ ID NO:10) and amino acid sequence (SEQ ID NO:11) of amino terminus of A/PR/8/34 hemagglutinin (HA) protein, including the cytoplasmic tail and transmembrane domains. The HA cytoplasmic tail (SNGSLQCRICI) is shown in bold and the transmembrane domain is underlined.

DETAILED DESCRIPTION

Figure 2:
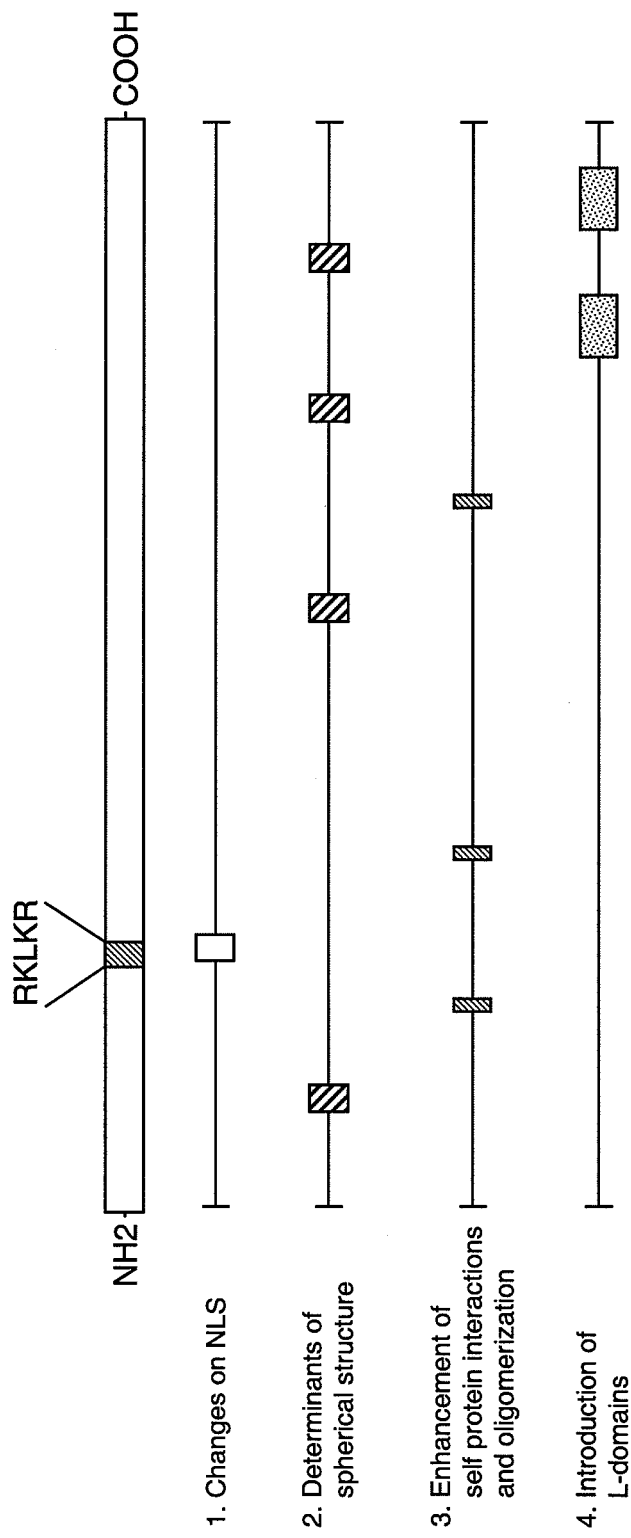
FIG. 2 is a schematic depicting exemplary amino acid sequence modifications to matrix protein 1 (M1). These modifications may enhance assembly and/or release of polyvalent influenza VLPs by cells transfected with constructs as described herein.

The practice of the present invention will employ, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, 18th Edition (Easton, Pa.: Mack Publishing Company, 1990); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); Sambrook, et al., Molecular Cloning: A Laboratory Manual (2nd Edition, 1989); Short Protocols in Molecular Biology, 4th ed. (Ausubel et al. eds., 1999, John Wiley & Sons); Molecular Biology Techniques: An Intensive Laboratory Course, (Ream et al., eds., 1998, Academic Press); PCR (Introduction to Biotechniques Series), 2nd ed. (Newton & Graham eds., 1997, Springer Verlag); Fundamental Virology, Second Edition (Fields & Knipe eds., 1991, Raven Press, New York).

All publications, patents and patent applications cited herein are hereby incorporated by reference in their entirety.

As used in this specification and the appended claims, the singular forms "a," "an" and "the" include plural references unless the content clearly dictates otherwise. Thus, for example, reference to "a VLP" includes a mixture of two or more such VLPs.

Definitions

As used herein, the terms "sub-viral particle" "virus-like particle" or "VLP" refer to a nonreplicating, viral shell, preferably derived from influenza virus proteins. VLPs are generally composed of one or more viral proteins, such as, but not limited to those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art and discussed more fully below. The presence of VLPs following recombinant expression of viral proteins can be detected using conventional techniques known in the art, such as by electron microscopy, biophysical characterization, and the like. See, e.g., Baker et al., *Biophys. J.* (1991) 60:1445-1456; Hagensee et al., *J. Virol.* (1994) 68:4503-4505. For example, VLPs can be isolated by density gradient centrifugation and/or identified by characteristic density banding (e.g., Examples). Alternatively, cryo-electron microscopy can be performed on vitrified aqueous samples of the VLP preparation in question, and images recorded under appropriate exposure conditions.

By "particle-forming polypeptide" derived from a particular viral protein is meant a full-length or near full-length viral protein, as well as a fragment thereof, or a viral protein with internal deletions, which has the ability to form VLPs under conditions that favor VLP formation. Accordingly, the polypeptide may comprise the full-length sequence, fragments, truncated and partial sequences, as well as analogs and precursor forms of the reference molecule. The term therefore intends deletions, additions and substitutions to the sequence, so long as the polypeptide retains the ability to form a VLP. Thus, the term includes natural variations of the specified polypeptide since variations in coat proteins often occur between viral isolates. The term also includes deletions, additions and substitutions that do not naturally occur in the reference protein, so long as the protein retains the ability to form a VLP. Preferred substitutions are those which are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids.

An "antigen" refers to a molecule containing one or more epitopes (either linear, conformational or both) that will stimulate a host's immune-system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term includes polypeptides which include modifications, such as deletions, additions and substitutions (generally conservative in nature) as compared to a native sequence, so long as the protein maintains the ability to elicit an immunological response, as defined herein. These modifications may be deliberate, as through site-directed mutagenesis, or may be accidental, such as through mutations of hosts which produce the antigens.

An "immunological response" to an antigen or composition is the development in a subject of a humoral and/or a cellular immune response to an antigen present in the composition of interest. For purposes of the present disclosure, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. Hence, an immunological response may include one or more of the following effects: the production of antibodies by B-cells; and/or the activation of suppressor T-cells and/or γΔ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic composition" is a composition that comprises an antigenic molecule where administration of the composition to a subject results in the development in the subject of a humoral and/or a cellular immune response to the antigenic molecule of interest.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences, see e.g., McCaughan et al. (1995) PNAS USA 92:5431-5435; Kochetov et al (1998) FEBS Letts. 440:351-355.

A "nucleic acid" molecule can include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also captures sequences that include any of the known base analogs of DNA and RNA.

"Operably linked" refers to an arrangement of elements wherein the components so described are configured so as to perform their usual function. Thus, a given promoter operably linked to a coding sequence is capable of effecting the expression of the coding sequence when active. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). Suitable programs for calculating the percent identity or similarity between sequences are generally known in the art.

A "vector" is capable of transferring gene sequences to target cells (e.g., bacterial plasmid vectors, viral vectors, non-viral vectors, particulate carriers, and liposomes). Typically, "vector construct," "expression vector," and "gene transfer vector," mean any nucleic acid construct capable of directing the expression of one or more sequences of interest in a host cell. Thus, the term includes cloning and expression vehicles, as well as viral vectors. The term is used interchangeable with the terms "nucleic acid expression vector" and "expression cassette."

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

General Overview

Described herein are polyvalent VLPs that can be used to protect humans from the predominantly circulating epidemic strains and may be readily reformulated to accommodate new antigenic drifts. The emergence of novel influenza viruses may result in strains completely unknown to the human immune system and, if transmissible, may result in a pandemic. For example, the avian influenza H5N1 virus has caused deadly outbreaks in avian and mammalian species (including humans) since 1997. This virus has evolved into two distinct phylogenetic clades—clade 1 viruses circulating in Cambodia, Thailand and Vietnam and clade 2 viruses which circulated in birds in China and Indonesia during 2003-2004, and spread west into Europe, Middle East and Africa, have been responsible for human infections during 2005 and 2006. However, because these viruses do not cross-neutralize, each one is independently able to cause severe and fatal cases of influenza in humans. Given the uncertainty as to which one of these viruses may ultimately acquire the ability to efficiently transmit among humans creates the dilemma as to which virus/es (Vietnam, clade1 or Indonesia clade 2) should be included in conventional, egg-produced vaccines.

Thus, the polyvalent VLPs described herein allow for protection of multiple influenza strains. These polyvalent virus-like particle (VLP) vaccines carry on their surfaces HA and/or NA molecules in any combination (e.g., representative of clade 1 and 2 of the H5N1 virus).

The polyvalent influenza virus-like particles (VLPs) described herein increase antigenic coverage, reduce development and manufacturing times, as well as costs. Production of our vaccine involves the use of cell based systems which yields safe (non-infectious) virus-like particles that maintain native antigenic epitopes because chemical inactivation is not required. The lack of need for chemical inactivation will also reduce production time and cost. In addition, influenza VLPs can be administered intranasally. See, e.g., Latham & Galarza (2001) J. Virol. 75(13):6154-6165; Galarza et al. (2005) Viral. Immunol. 18(1):244-51; and U.S. Patent Publication 200550186621.

Advantages of the present disclosure include (i) rapid and flexible cloning methods for influenza vaccine development, (ii) cell-based influenza vaccine production system, (ii) non-infectious (safe) virus-like particles vaccines that do not require inactivation, (iii) two or more antigenically distinct component in one preparation, and (iv) intranasal immunization.

Virus-Like Particles

When sequences encoding influenza proteins are expressed in eukaryotic, the proteins have been shown to self-assemble into noninfectious virus-like particles (VLP). See, Latham & Galarza (2001) J. Virol. 75(13):6154-6165; Galarza et al. (2005) Viral. Immunol. 18(1):244-51; and U.S. Patent Publications 200550186621 and 20060263804.

The present disclosure relates to the assembly and release of polyvalent influenza VLPs from the plasma membrane of eukaryotic cells, which VLPs carry on their surfaces two or more antigenically distinct surface glycoproteins. This polyvalent VLP, alone or in combination with one or more adjuvants, stimulates an immune response that protects against infection with any of the antigenically distinct influenza viruses or viral pathogens from which the surface antigens were derived.

The polyvalent VLP (also called sub-viral structure vaccine (SVSV)) is composed of viral proteins produced from naturally occurring and/or mutated nucleic acid sequences of genes coding for matrix protein M1 and two or more antigenically distinct surface glycoproteins derived from different viruses and containing engineered unique structural motifs for optimal molecular contacts with the oligomerized matrix protein M1 scaffold. The matrix protein M1 is a universal component for the formation of all possible polyvalent sub-viral structure vaccine combinations. An M2 protein is optionally included may or may not be part of the sub-viral structure and its incorporation depends on the desired antigenic composition of the final vaccine product. When present, the M2 protein may be modified as described herein.

Antigenically distinct glycoproteins derived from the same or different families of enveloped viruses can be selected for incorporation onto the surface of the vaccine. The incorporation of antigenically distinct viral glycoproteins into the same vaccine particle can be facilitated by replacing the cytoplasmic tail and transmembrane amino acid sequences with those from a common glycoprotein via alterations in the nucleic acids coding for these proteins. This approach allows for the design of a large number of possible polyvalent sub-viral vaccine combinations.

1. Influenza Polypeptide-Encoding Sequences

The VLPs produced as described herein are conveniently prepared using standard recombinant techniques. Polynucleotides encoding the influenza proteins are introduced into a host cell and, when the influenza proteins are expressed in the cell, they assembly into VLPs.

Polynucleotide sequences coding for molecules (structural and/or antigen polypeptides) that form and/or incorporate into the VLPs can be obtained using recombinant methods, such as by screening cDNA and genomic libraries from cells expressing the gene, or by deriving the gene from a vector known to include the same. For example, plasmids which contain sequences that encode naturally occurring or altered cellular products may be obtained from a depository such as the A.T.C.C., or from commercial sources. Plasmids containing the nucleotide sequences of interest can be digested with appropriate restriction enzymes, and DNA fragments containing the nucleotide sequences can be inserted into a gene transfer vector using standard molecular biology techniques.

Alternatively, cDNA sequences may be obtained from cells which express or contain the sequences, using standard techniques, such as phenol extraction and PCR of cDNA or genomic DNA. See, e.g., Sambrook et al., supra, for a description of techniques used to obtain and isolate DNA. Briefly, mRNA from a cell which expresses the gene of interest can be reverse transcribed with reverse transcriptase using oligo-dT or random primers. The single stranded cDNA may then be amplified by PCR (see U.S. Pat. Nos. 4,683,202, 4,683,195 and 4,800,159, see also PCR Technology: Principles and Applications for DNA Amplification, Erlich (ed.), Stockton Press, 1989)) using oligonucleotide primers complementary-to sequences on either side of desired sequences.

The nucleotide sequence of interest can also be produced synthetically, rather than cloned, using a DNA synthesizer (e.g., an Applied Biosystems Model 392 DNA Synthesizer, available from ABI, Foster City, Calif.). The nucleotide sequence can be designed with the appropriate codons for the expression product desired. The complete sequence is assembled from overlapping oligonucleotides prepared by standard methods and assembled into a complete coding sequence. See, e.g., Edge (1981) Nature 292:756; Nambair et al. (1984) Science 223:1299; Jay et al. (1984) J. Biol. Chem. 259:6311.

The influenza VLPs described herein are typically formed by expressing sequences encoding M1 and two or more antigenic influenza glycoproteins (HA and NA) in a host cell. The VLPs may optionally comprise M2. The expressed proteins self-assemble into VLPs with the antigenic glycoproteins decorating the surface of the VLP.

The sequences can be derived from any two influenza strains, preferably influenza A strains or two different influenza B strains. There are three types of influenza viruses: A, B, and C. Influenza A viruses are further classified by subtype on the basis of the two main surface glycoproteins hemagglutinin (HA) and neuraminidase (NA) (e.g., H1N1, H1N2, H3N2, H3N5, etc.). There are 16 known HA subtypes (H1, H2, H3, H4, H5, H6, H7, H8, H9, H10, H11, H12, H13, H14, H15, H16) and 9 known NA subtypes (N1, N2, N3, N4, N5, N6, N7, N8, N9). The VLPs described herein can include any combination of these 16 HA subtypes and/or these 9 NA subtypes.

As hundreds of strains of influenza viruses have been identified and are continually being identified, it will be apparent that glycoproteins from any of these strains can be incorporated into the VLPs described herein. Examples of strains from which influenza encoding sequences can be derived include those listed by the World Health Organizations and the Centers for Disease Control (CDC) (both organizations maintain lists of pathogenic strains which are available on the internet). Non-limiting examples of such influenza strains include: A/Puerto Rico/8/34 (H1N1), A/Asian/57 (H2N2), A/Hong Kong/68 (H3N2), A/New York/55/04 (H3N2), A/Vietnam/1203/04 (H5N1)

The polyvalent VLPs described herein incorporate any combination of HA and/or NA antigenic polypeptides from different strains or subtypes. Furthermore, it will be apparent that antigenic drift and antigenic shift occur in flu viruses, resulting in new strains. When a new strain of human influenza virus emerges, antibody protection that may have developed after infection or vaccination with an older strain may not provide protection against the new strain. Therefore, the disclosure contemplates use of sequences from both identified and unidentified strains in the formation of polyvalent VLPs. See, also the internet for updated virus listings, for example the World Health Organization site referenced above.

The VLPs described herein may further comprise an influenza nucleoprotein (NP) and/or at least one protein of the polymerase complex, i.e., one or more of PB1, PB2 and PA (e.g., PB1, PB2, and PA; PB1 and PB2; PB1 and PA; PB2 and PA). Preferably, the VLPs do not include NP and all three proteins of the polymerase complex. The structure and function of influenza NP and polymerase complex proteins is known and described for example on pages 428 to 432 of Kuby Immunology, 4$^{th}$ ed. (Goldsby et al. eds.) WH Freeman & Company, New York.

The sequences may be naturally occurring sequences or, alternatively, may include modifications, made using standard molecular biological techniques, for example to enhance expression, interaction with other proteins (e.g., M1), etc. See, Examples.

The polyvalent influenza VLP are typically formed by expressing one or more influenza matrix proteins and one or more antigenic influenza glycoproteins (HA and NA).

In certain embodiments, the sequences encode naturally occurring or modified M1 and/or M2 are selected for use. The sequences encoding the matrix protein(s) may be derived from any influenza virus, for example from the influenza virus strain A/PR/8 (H1N1) or influenza strain A/Udorn/72 (H3N2). Exemplary modifications, with respect to the matrix proteins of A/Udorn/72 are shown in Tables 1 and 2 below.

TABLE 1

| M1 Domain | Residues* | Exemplary Changes |
|---|---|---|
| NLS | 101-105 | Deletion, insertion and/or substition of one or more residues |
| spherical structure determinants | 41 | deletion and/or substitution of residues and/or one or more surrounding residues |
|  | 95 |  |
|  | 98 |  |
|  | 167 |  |
|  | 204 |  |
|  | 205 |  |
|  | 218 |  |
| self and oligomerization domains | 4 | Deletion, insertion and/or substitution of one or more residues |
|  | 16 |  |
|  | 19 |  |
|  | 33 |  |
|  | 50 |  |
|  | 51 |  |
|  | 52 |  |
|  | 59 |  |
|  | 66 |  |
|  | 67 |  |
| L-domains | Self 100-103 or from other viruses | introduce L-domains as additions or instead of native sequences |

*numbered relative to 252 amino acid sequence of A/Udorn/72 M1 as shown in GenBank Accession No. ABD79033

TABLE 2

| M2 Domain | Residues* | Exemplary Changes |
|---|---|---|
| L-domains | 100-103 from M1 or L domains from other viruses | introduce L-domains as additions or instead of native sequences |
| Addition of sequences encoding immunomodulators | C- or N-terminus | addition of sequences encoding immunomodulators (e.g., adjuvants) |

*numbered relative to 96 amino acid sequence of A/Udorn/72 M2 shown in GenBank Accession No. ABD79034

The matrix proteins of various influenza proteins are typically fairly conserved and one of skill in the art can readily align sequences from any given strains to determine domains and regions corresponding to the those set forth above.

Thus, as shown above, in certain embodiments, the M1 protein contains one or more modifications shown in Table 1. For example, the nuclear localization signal (NLS), one or more determinants of spherical structure (e.g., amino acid residues 41, 95, 98, 167, 204, 205 and 218, numbered relative to A/Udorn/72); one or more regions involved in self-protein interactions and/or oligomerization may be modified; and/or one or more L-domains may be introduced. See, FIG. 2. L-domains are specific motifs that interact with cellular components which are recruited for budding and pinching off of the virus or virus-like particles from the cell membrane. L-domains of certain viruses are able to function in a position independent manner and some of them are functionally interchangeable among different viruses. Hui et al. (2003) *J. Virol.* 77:7078-7092; Hui et. al. (2006), *J. Virol.* 80:2291-2308; Freed, E. O. (2002) *J. Virol.* 76:4679-4687

During viral infection, a significant proportion of the synthesized matrix protein translocates to the nucleus of the infected cells where it participates in ribonucleoprotein (RNP) translocation to the cytoplasm and transport to the cell periphery for virus assembly and budding. A smaller fraction of produced matrix protein directly associates with the plasma membrane and is the driving force in virus assembly and budding. When matrix protein is expressed in eukaryotic cells alone or in combination with other viral structural proteins it demonstrates a similar distribution pattern as in infected cells. Modification of the nuclear localization signal alters this distribution pattern by diverting most of the matrix protein to the cell periphery where it associates with the inner leaflet of the plasma membrane enhancing protein-protein interaction and self oligomerization leading to greater frequency of sub-viral particle assembly and release. Thus, such changes may enhance the efficiency of sub-viral structure assembly and release, therefore increasing vaccine production yield.

Sequences encoding HA and/or NA glycoproteins are also provided and are incorporate into the influenza VLPs such that they are expressed on the surface. The sequences encoding the glycoprotein(s) may be naturally occurring or modified (e.g., by deletions, additions and/or substitutions) (see, Examples).

In certain embodiments, the sequences encode chimeric polypeptides, for example chimeric glycoproteins (HA and/or NA) or hybrid matrix-immunomodulatory polypeptides are used in constructing a VLP. It will be apparent that all or parts of the polypeptides may be replaced with sequences from other viruses and/or sequences from other influenza strains. In a preferred embodiment, the sequences encoding the HA and/or NA glycoproteins are chimeric in that they include heterologous sequences encoding the transmembrane and/or cytoplasmic tail domains. See, FIGS. 4 and 11-14. For example, the transmembrane domain and cytoplasmic tail of both HA5 and HA 1918 may be replaced by the homologous domains derived from influenza A/Udorn/72 or A/PR/8/34. The HA molecule is a type I glycoprotein, thus the transmembrane and cytoplasmic tail exchanged are located at the carboxyl-terminal ($COOH_2$) end of the molecule. In the case of NA, a type II glycoprotein, the exchanged domains are located at the amino-terminal ($NH_2$) end of the molecule. These exchanges enhance the interaction of the surface glycoproteins with the scaffold formed by the matrix protein M1, which is also derived from either influenza A/Udorn/72 or A/PR/8/34 virus and underlies the membrane of the sub-viral structure. See, FIGS. 11 to 14

Preferably, the influenza sequences employed to form influenza VLPs exhibit between about 60% to 80% (or any value therebetween including 61%, 62%, 63%, 64%, 65%, 66%, 67%, 68%, 69%, 70%, 71%, 72%, 73%, 74%, 75%, 76%, 77%, 78% and 79%) sequence identity to a naturally occurring influenza polynucleotide sequence and more preferably the sequences exhibit between about 80% and 100% (or any value therebetween including 81%, 82%, 83%, 84%, 85%, 86%, 87%, 88%, 89%, 90%, 91%, 92%, 93%, 94%, 95%, 96%, 97%, 98% and 99%) sequence identity to a naturally occurring influenza polynucleotide sequence.

Any of the sequences described herein may further include additional sequences. For example, to further to enhance vaccine potency, hybrid molecules are expressed and incorporated into the sub-viral structure. These hybrid molecules are generated by linking, at the DNA level, the sequences coding for the matrix protein genes with sequences coding for an adjuvant or immuno-regulatory moiety. During sub-viral structure formation, these chimeric proteins are incorporated into or onto the particle depending on whether M1 or optional M2 carries the adjuvant molecule. The incorporation of one or more polypeptide immunomodulatory polypeptides (e.g., adjuvants describe in detail below) into the sequences described herein into the VLP may enhance potency and therefore reduces the amount of antigen required for stimulating a protective immune response. Alternatively, as described below, one or more additional molecules (polypeptide or small molecules) may be included in the VLP-containing compositions after production of the VLP from the sequences described herein.

These sub-viral structures do not contain infectious viral nucleic acids and they are not infectious eliminating the need for chemical inactivation. Absence of chemical treatment preserves native epitopes and protein conformations enhancing the immunogenic characteristics of the vaccine.

The sequences described herein can be operably linked to each other in any combination. For example, one or more sequences may be expressed from the same promoter and/or from different promoters. As described below, sequences may be included on one or more vectors.

The polyvalent VLPs described herein comprise multiple copies of antigenic flu proteins (e.g., HA and/or NA) from two or more different influenza strains.

2. Expression Vectors

Once the constructs comprising the sequences encoding the influenza polypeptides desired to be incorporated into the VLP have been synthesized, they can be cloned into any suitable vector or replicon for expression. Numerous cloning vectors are known to those of skill in the art, and one having ordinary skill in the art can readily select appropriate vectors and control elements for any given host cell type in view of the teachings of the present specification and information known in the art about expression. See, generally, Ausubel et al, supra or Sambrook et al, supra.

Non-limiting examples of vectors that can be used to express sequences that assembly into VLPs as described herein include viral-based vectors (e.g., retrovirus, adenovirus, adeno-associated virus, lentivirus), baculovirus vectors (see, Examples), plasmid vectors, non-viral vectors, mammalians vectors, mammalian artificial chromosomes (e.g., liposomes, particulate carriers, etc.) and combinations thereof.

The expression vector(s) typically contain(s) coding sequences and expression control elements which allow expression of the coding regions in a suitable host. The control elements generally include a promoter, translation initiation codon, and translation and transcription termination sequences, and an insertion site for introducing the insert into the vector. Translational control elements have been reviewed by M. Kozak (e.g., Kozak, M., Mamm. Genome 7(8):563-574, 1996; Kozak, M., Biochimie 76(9):815-821, 1994; Kozak, M., J Cell Biol 108(2):229-241, 1989; Kozak, M., and Shatkin, A. J., Methods Enzymol 60:360-375, 1979).

For example, typical promoters for mammalian cell expression include the SV40 early promoter, a CMV promoter such as the CMV immediate early promoter (a CMV promoter can include intron A), RSV, HIV-LTR, the mouse mammary tumor virus LTR promoter (MMLV-LTR), FIV-LTR, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook, et al., supra, as well as a bovine growth hormone terminator sequence. Introns, containing splice donor and acceptor sites, may also be designed into the constructs as described herein (Chapman et al., Nuc. Acids Res. (1991) 19:3979-3986).

Enhancer elements may also be used herein to increase expression levels of the mammalian constructs. Examples include the SV40 early gene enhancer, as described in Dijkema et al., EMBO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence (Chapman et al., Nuc. Acids Res. (1991) 19:3979-3986).

It will be apparent that one or more vectors may contain one or more sequences encoding proteins to be incorporated into the VLP. For example, a single vector may carry sequences encoding all the proteins found in the VLP. Alternatively, multiple vectors may be used (e.g., multiple constructs, each encoding a single polypeptide-encoding sequence or multiple constructs, each encoding one or more polypeptide-encoding sequences). In embodiments in which a single vector comprises multiple polypeptide-encoding sequences, the sequences may be operably linked to the same or different transcriptional control elements (e.g., promoters) within the same vector.

In addition, one or more sequences encoding non-influenza proteins may be expressed and incorporated into the VLP, including, but not limited to, sequences comprising and/or encoding immunomodulatory molecules (e.g., adjuvants described below), for example, immunomodulating oligonucleotides (e.g., CpGs), cytokines, detoxified bacterial toxins and the like.

3. VLP Production

As noted above, influenza proteins expressed in a eukaryotic host cell have been shown to self-assemble into noninfectious virus-like particles (VLP). Accordingly, the sequences and/or vectors described herein are then used to transform an appropriate host cell. The construct(s) encoding the proteins that form the VLPs described herein provide efficient means for the production of influenza VLPs using a variety of different cell types, including, but not limited to, insect, fungal (yeast) and mammalian cells.

Preferably, the sub-viral structure vaccines are produced in eukaryotic cells following transfection, establishment of continuous cell lines (using standard protocols) and/or infection with DNA constructs that carry the influenza genes of interest as known to one skilled in the art. The level of expression of the proteins required for sub-viral structure formation is maximized by sequence optimization of the eukaryotic or viral promoters that drive transcription of the selected genes. The sub-viral structure vaccine is released into the culture medium, from where it is purified and subsequently formulated as a vaccine. The sub-viral structures are not infectious and therefore inactivation of the VLP is not required as it is for some killed viral vaccines The ability of influenza polypeptides expressed from sequences as described herein to self-assemble into VLPs with antigenic glycoproteins presented on the surface allows these VLPs to be produced in many host cell by co-introduction of the desired sequences. The sequence(s) (e.g., in one or more expression vectors) may be stably and/or transiently integrated in various combinations into a host cell.

Suitable host cells include, but are not limited to, bacterial, mammalian, baculovirus/insect, yeast, plant and *Xenopus* cells.

For example, a number of mammalian cell lines are known in the art and include primary cells as well as immortalized cell lines available from the American Type Culture Collection (A.T.C.C.), such as, but not limited to, BHK, VERO, MRC-5, WI-38, HT1080, 293, 293T, RD, COS-7, CHO, Jurkat, HUT, SUPT, C8166, MOLT4/clone8, MT-2, MT-4, H9, PM1, CEM, myeloma cells (e.g., SB20 cells) and CEMX174 (such cell lines are available, for example, from the A.T.C.C.).

Similarly, bacterial hosts such as *E. coli, Bacillus subtilis*, and *Streptococcus* spp., will find use with the present expression constructs.

Yeast hosts useful in the present disclosure include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Fungal hosts include, for example, *Aspergillus*.

Insect cells for use with baculovirus expression vectors include, inter alia, *Aedes aegypti, Autographa californica, Bombyx mori, Drosophila melanogaster, Spodoptera frugiperda*, and *Trichoplusia ni*. See, Latham & Galarza (2001) *J. Virol.* 75(13):6154-6165; Galarza et al. (2005) *Viral. Immunol.* 18(1):244-51; and U.S. Patent Publications 200550186621 and 20060263804.

Cell lines expressing one or more of the sequences described above can readily be generated given the disclosure provided herein by stably integrating one or more expression vector constructs encoding the influenza proteins of the VLP. The promoter regulating expression of the stably integrated influenza sequences (s) may be constitutive or inducible. Thus, a cell line can be generated in which one or more both of the matrix proteins are stably integrated such that, upon introduction of the influenza glycoprotein-encoding sequences described herein (e.g., chimeric glycoproteins) into a host cell and expression of the influenza proteins encoded by the polynucleotides, non-replicating influenza viral particles that present antigenic glycoproteins are formed.

In certain embodiments, a mammalian cell line that stably expressed two or more antigenically distinct influenza glycproteins is generated. Sequences encoding M1, M2 and/or additional glycoproteins (e.g., from the same or different virus strains) can be introduced into such a cell line to produce VLPs as described herein. Alternatively, a cell line that stably produces an influenza M1 protein (and, optionally, M2) can be generated and sequences encoding the glycoprotein(s) from the selected influenza strain introduced into the cell line, resulting in production of VLPs presenting the desired antigenic glycoproteins.

The parent cell line from which an influenza VLP-producer cell line is derived can be selected from any cell described above, including for example, mammalian, insect, yeast, bacterial cell lines. In a preferred embodiment, the cell line is a mammalian cell line (e.g., 293, RD, COS-7, CHO, BHK, MDCK, MDBK, MRC-5, VERO, HT1080, and myeloma cells). Production of influenza VLPs using mammalian cells provides (i) VLP formation; (ii) correct post translation modifications (glycosylation, palmitylation) and budding; (iii) absence of non-mammalian cell contaminants and (iv) ease of purification.

In addition to creating cell lines, influenza-encoding sequences may also be transiently expressed in host cells. Suitable recombinant expression host cell systems include, but are not limited to, bacterial, mammalian, baculovirus/ insect, vaccinia, Semliki Forest virus (SFV), Alphaviruses (such as, Sindbis, Venezuelan Equine Encephalitis (VEE)), mammalian, yeast and *Xenopus* expression systems, well known in the art. Particularly preferred expression systems are mammalian cell lines, vaccinia, Sindbis, insect and yeast systems.

Many suitable expression systems are commercially available, including, for example, the following: baculovirus expression (Reilly, P. R., et al., BACULOVIRUS EXPRESSION VECTORS: A LABORATORY MANUAL (1992); Beames, et al., Biotechniques 11:378 (1991); Pharmingen; Clontech, Palo Alto, Calif.)), vaccinia expression systems (Earl, P. L., et al., "Expression of proteins in mammalian cells using vaccinia" In Current Protocols in Molecular Biology (F. M. Ausubel, et al. Eds.), Greene Publishing Associates & Wiley Interscience, New York (1991); Moss, B., et al., U.S. Pat. No. 5,135,855, issued Aug. 4, 1992), expression in bacteria (Ausubel, F. M., et al., CURRENT PROTOCOLS IN MOLECULAR BIOLOGY, John Wiley and Sons, Inc., Media Pa.; Clontech), expression in yeast (Rosenberg, S, and Tekamp-Olson, P., U.S. Pat. No. RE35,749, issued, Mar. 17, 1998, herein incorporated by reference; Shuster, J. R., U.S. Pat. No. 5,629,203, issued May 13, 1997, herein incorporated by reference; Gellissen, G., et al., Antonie Van Leeuwenhoek, 62(1-2):79-93 (1992); Romanos, M. A., et al., Yeast 8(6):423-488 (1992); Goeddel, D. V., Methods in Enzymology 185 (1990); Guthrie, C., and G. R. Fink, Methods in Enzymology 194 (1991)), expression in mammalian cells (Clontech; Gibco-BRL, Ground Island, N.Y.; e.g., Chinese hamster ovary (CHO) cell lines (Haynes, J., et al., Nuc. Acid. Res. 11:687-706 (1983); 1983, Lau, Y. F., et al., Mol. Cell. Biol. 4:1469-1475 (1984); Kaufman, R. J., "Selection and coamplification of heterologous genes in mammalian cells," in Methods in Enzymology, vol. 185, pp 537-566. Academic Press, Inc., San Diego Calif. (1991)), and expression in plant cells (plant cloning vectors, Clontech Laboratories, Inc., Palo-Alto, Calif., and Pharmacia LKB Biotechnology, Inc., Pistcataway, N.J.; Hood, E., et al., J. Bacteriol. 168:1291-1301 (1986); Nagel, R., et al., FEMS Microbiol. Lett. 67:325 (1990); An, et al., "Binary Vectors", and others in Plant Molecular Biology Manual A3:1-19 (1988); Miki, B. L. A., et al., pp. 249-265, and others in Plant DNA Infectious Agents (Hohn, T., et al., eds.) Springer-Verlag, Wien, Austria, (1987); Plant Molecular Biology: Essential Techniques, P. G. Jones and J. M. Sutton, New York, J. Wiley, 1997; Miglani, Gurbachan Dictionary of Plant Genetics and Molecular Biology, New York, Food Products Press, 1998; Henry, R. J., Practical Applications of Plant Molecular Biology, New York, Chapman & Hall, 1997).

When expression vectors containing the altered genes that code for the proteins required for sub-viral structure vaccine formation are introduced into host cell(s) and subsequently expressed at the necessary level, the sub-viral structure vaccine assembles and is then released from the cell surface into the culture media (FIG. 7).

Depending on the expression system and host selected, the VLPs are produced by growing host cells transformed by an expression vector under conditions whereby the particle-forming polypeptide is expressed and VLPs can be formed. The selection of the appropriate growth conditions is within the skill of the art. If the VLPs are formed and retained intracellularly, the cells are then disrupted, using chemical, physical or mechanical means, which lyse the cells yet keep the VLPs substantially intact. Such methods are known to those of skill in the art and are described in, e.g., Protein Purification Applications: A Practical Approach, (E. L. V. Harris and S. Angal, Eds., 1990). Alternatively, VLPs may be secreted and harvested from the surrounding culture media.

The particles are then isolated (or substantially purified) using methods that preserve the integrity thereof, such as, by density gradient centrifugation, e.g., sucrose gradients, PEG-precipitation, pelleting, and the like (see, e.g., Kirnbauer et al. J. Virol. (1993) 67:6929-6936), as well as standard purification techniques including, e.g., ion exchange and gel filtration chromatography.

Compositions

VLPs produced as described herein can be used to elicit an immune response when administered to a subject. As discussed above, the VLPs can comprise a variety of antigens (e.g., one or more influenza antigens from one or more strains or isolates). Purified VLPs can be administered to a vertebrate subject, usually in the form of vaccine compositions. Combination vaccines may also be used, where such vaccines contain, for example, other subunit proteins derived from influenza or other organisms and/or gene delivery vaccines encoding such antigens.

VLP immune-stimulating (or vaccine) compositions can include various excipients, adjuvants, carriers, auxiliary substances, modulating agents, and the like. The immune stimulating compositions will include an amount of the VLP/antigen sufficient to mount an immunological response. An appropriate effective amount can be determined by one of skill in the art. Such an amount will fall in a relatively broad range that can be determined through routine trials and will generally be an amount on the order of about 0.1 μg to about 10 (or more) mg, more preferably about 1 μg to about 300 μg, of VLP/antigen.

Sub-viral structure vaccines are purified from the cell culture medium and formulated with the appropriate buffers and additives, such as a) preservatives or antibiotics; b) stabilizers, including proteins or organic compounds; c) adjuvants or immuno-modulators for enhancing potency and modulating immune responses (humoral and cellular) to the vaccine; or d) molecules that enhance presentation of vaccine antigens to specifics cell of the immune system. This vaccine can be prepared in a freeze-dried (lyophilized) form in order to provide for appropriate storage and maximize the shelf-life of the preparation. This will allow for stock piling of vaccine for prolonged periods of time maintaining immunogenicity, potency and efficacy.

A carrier is optionally present in the compositions described herein. Typically, a carrier is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; McGee J P, et al., J. Microencapsul.

14(2):197-210, 1997; O'Hagan D T, et al., Vaccine 11(2):149-54, 1993. Such carriers are well known to those of ordinary skill in the art.

Additionally, these carriers may function as immunostimulating agents ("adjuvants"). Exemplary adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detoxu); (3) saponin adjuvants, such as Stimulom™. (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), beta chemokines (MIP, 1-alpha, 1-beta Rantes, etc.); (6) detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetyl-muramyl-L-alanyl-D-isogluatminyl-L-alanine-2-(1'-2'-dipalmitoyl-sn-glycero-3-huydroxyphosphoryloxy)-ethylamine (MTP-PE), etc.

Examples of suitable immunomodulatory molecules for use herein include adjuvants described above and the following: IL-1 and IL-2 (Karupiah et al. (1990) J. Immunology 144:290-298, Weber et al. (1987) J. Exp. Med. 166:1716-1733, Gansbacher et al. (1990) J. Exp. Med. 172:1217-1224, and U.S. Pat. No. 4,738,927-); IL-3 and IL-4 (Tepper et al. (1989) Cell 57:503-512, Golumbek et al. (1991) Science 254:713-716, and U.S. Pat. No. 5,017,691); IL-5 and IL-6 (Brakenhof et al. (1987) J. Immunol. 139:4116-4121, and International Publication No. WO 90/06370); IL-7 (U.S. Pat. No. 4,965,195); IL-8, IL-9, IL-10, IL-11, IL-12, and IL-13 (Cytokine Bulletin, Summer 1994); IL-14 and IL-15; alpha interferon (Finter et al. (1991) Drugs 42:749-765, U.S. Pat. Nos. 4,892,743 and 4,966,843, International Publication No. WO 85/02862, Nagata et al. (1980) Nature 284:316-320, Familletti et al. (1981) Methods in Enz. 78:387-394, Twu et al. (1989) Proc. Natl. Acad. Sci. USA 86:2046-2050, and Faktor et al. (1990) Oncogene 5:867-872); β-interferon (Seif et al. (1991) J. Virol. 65:664-671); γ-interferons (Watanabe et al. (1989) Proc. Natl. Acad. Sci. USA 86:9456-9460, Gansbacher et al. (1990) Cancer Research 50:7820-7825, Maio et al. (1989) Can. Immunol. Immunother. 30:34-42, and U.S. Pat. Nos. 4,762,791 and 4,727,138); G-CSF (U.S. Pat. Nos. 4,999,291 and 4,810,643); GM-CSF (International Publication No. WO 85/04188); tumor necrosis factors (TNFs) (Jayaraman et al. (1990) J. Immunology 144:942-951); CD3 (Krissanen et al. (1987) Immunogenetics 26:258-266); ICAM-1 (Altman et al. (1989) Nature 338:512-514, Simmons et al. (1988) Nature 331:624-627); ICAM-2, LFA-1, LFA-3 (Wallner et al. (1987) J. Exp. Med. 166:923-932); MHC class I molecules, MHC class II molecules, B7.1-β2-microglobulin (Pames et al. (1981) Proc. Natl. Acad. Sci. USA 78:2253-2257); chaperones such as calnexin; and MHC-linked transporter proteins or analogs thereof (Powis et al. (1991) Nature 354:528-531). Immunomodulatory factors may also be agonists, antagonists, or ligands for these molecules. For example, soluble forms of receptors can often behave as antagonists for these types of factors, as can mutated forms of the factors themselves.

Nucleic acid molecules that encode the above-described substances, as well as other nucleic acid molecules that are advantageous for use within the present invention, may be readily obtained from a variety of sources, including, for example, depositories such as the American Type Culture Collection, or from commercial sources such as British Bio-Technology Limited (Cowley, Oxford England). Representative examples include BBG 12 (containing the GM-CSF gene coding for the mature protein of 127 amino acids), BBG 6 (which contains sequences encoding gamma interferon), A.T.C.C. Deposit No. 39656 (which contains sequences encoding TNF), A.T.C.C. Deposit No. 20663 (which contains sequences encoding alpha-interferon), A.T.C.C. Deposit Nos. 31902, 31902 and 39517 (which contain sequences encoding beta-interferon), A.T.C.C. Deposit No. 67024 (which contains a sequence which encodes Interleukin-1b), A.T.C.C. Deposit Nos. 39405, 39452, 39516, 39626 and 39673 (which contain sequences encoding Interleukin-2), A.T.C.C. Deposit Nos. 59399, 59398, and 67326 (which contain sequences encoding Interleukin-3), A.T.C.C. Deposit No. 57592 (which contains sequences encoding Interleukin-4), A.T.C.C. Deposit Nos. 59394 and 59395 (which contain sequences encoding Interleukin-5), and A.T.C.C. Deposit No. 67153 (which contains sequences encoding Interleukin-6).

Plasmids encoding one or more of the above-identified polypeptides can be digested with appropriate restriction enzymes, and DNA fragments containing the particular gene of interest can be inserted into a gene transfer vector (e.g., expression vector as described above) using standard molecular biology techniques. (See, e.g., Sambrook et al., supra, or Ausubel et al. (eds) Current Protocols in Molecular Biology, Greene Publishing and Wiley-Interscience).

Administration

The VLPs and compositions comprising these VLPs can be administered to a subject by any mode of delivery, including, for example, by parenteral injection (e.g. subcutaneously, intraperitoneally, intravenously, intramuscularly, or to the interstitial space of a tissue), or by rectal, oral (e.g. tablet, spray), vaginal, topical, transdermal (e.g. see WO99/27961) or transcutaneous (e.g. see WO02/074244 and WO02/064162), intranasal (e.g. see WO03/028760), ocular, aural, pulmonary or other mucosal administration. Multiple doses can be administered by the same or different routes. In a preferred embodiment, the doses are intranasally administered.

The VLPs (and VLP-containing compositions) can be administered prior to, concurrent with, or subsequent to delivery of other vaccines. Also, the site of VLP administration may be the same or different as other vaccine compositions that are being administered.

Dosage treatment with the VLP composition may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1-4 months for a second dose, and if needed, a subsequent dose(s) after several months. The dosage regimen will also, at least in part, be determined by the potency of the modality, the vaccine delivery employed, the need of the subject and be dependent on the judgment of the practitioner.

All patents, patent applications and publications mentioned herein are hereby incorporated by reference in their entireties.

Although disclosure has been provided in some detail by way of illustration and example for the purposes of clarity and understanding, it will be apparent to those of skill in the art that various changes and modifications can be practiced without departing from the spirit or scope of the disclosure. Accordingly, the foregoing disclosure and following examples should not be construed as limiting. For instance, although the VLPs disclosed in the Examples include M2, it will be apparent from the above disclosure that M2 is optional and that influenza VLPs as described herein can be formed without M2. See, also, U.S. Patent Publication Nos. 20050186621 and 20060263804.

EXAMPLES

Example 1

Polyvalent HA Influenza VLPs

Figure 5:
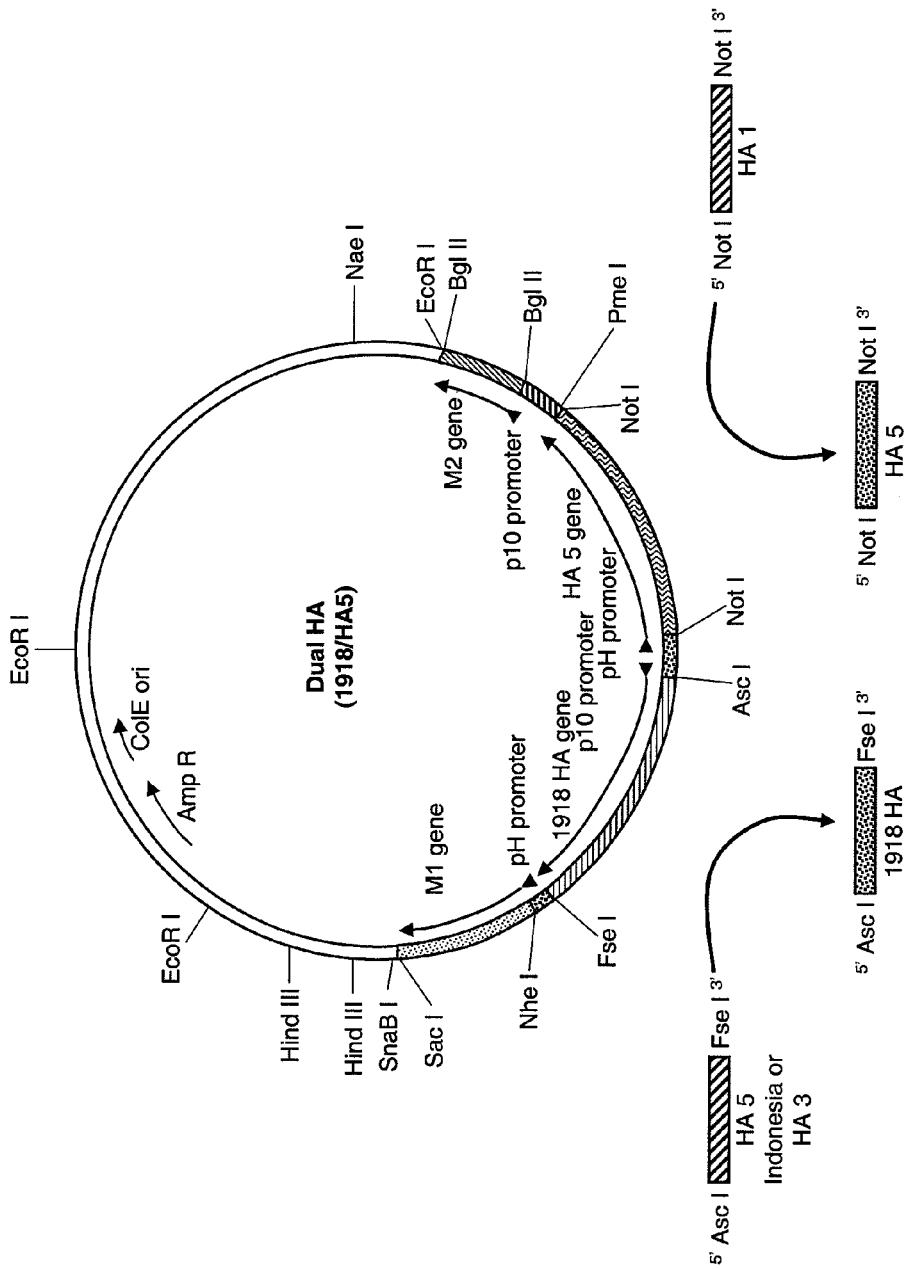
FIG. 5 is a schematic diagram of a baculovirus transfer vector carrying two antigenically distinct HA molecules.

To evaluate the formation of polyvalent influenza VLPs, the HA5 gene derived from the human influenza virus A/Vietnam/1203/2004 (H5N1) was obtained by RT-PCR from the reassortant virus A/VNH5N1-PR8/CDC-RG reference strain and the gene encoding the 1918 HA (A/South Caroline/1/18 (H1N1) was in vitro synthesized following the database sequence (accession #AF117241). Both genes were cloned into the pAcAB4 baculovirus transfer vector (Latham & Galarza (2001) *J. Virol.* 75(13):6154-6165; Galarza et al. (2005) *Viral. Immunol.* 18(1):244-51; and U.S. Patent Publication 200550186621). This vector contains the genes encoding the M1 and M2 proteins of the influenza virus A/Udorn/72 (H3N2). In this plasmid, the HA5 and M1 genes were under the transcriptional control of the baculovirus polyhedrin promoter and in opposite orientation, whereas the 1918 HA and the M2 were under the transcriptional control of the p10 promoter and in opposite orientation to each other (FIG. 5). In this construct, the cytoplasmic tail and transmembrane domain of both HAs were replaced with the homologous domains of the HA of the influenza virus A/Udorn/72. Recombinant virus was generated by co-transfecting Sf9 insect cells with transfer vector and a linear baculovirus genomic DNA.

Influenza-virus-like particles (VLPs) were produced by infecting Sf9 cells with the quadruple recombinant. Infection was allowed to proceed for 72 hrs at which time culture supernatant was collected, clarified, concentrated by high speed centrifugation and further purified by gradient centrifugation.

Western Blot/Immunoprecipitation

Figure 6A:
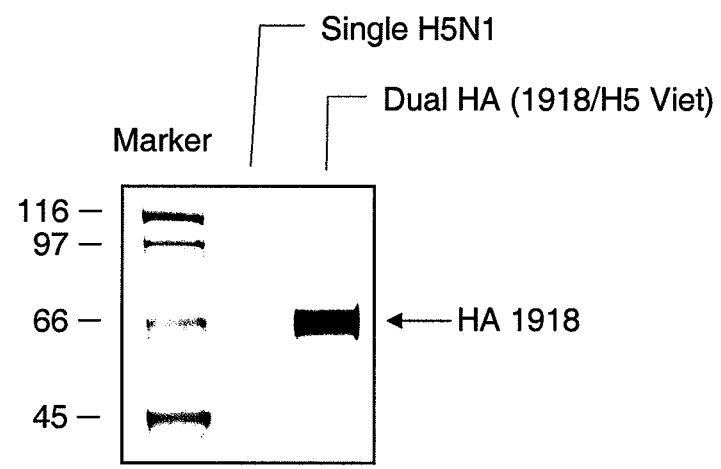
FIG. 6A shows that the VLPs comprise HA 1918 and FIG. 6B shows that the VLPs comprise HA5 Vietnam and M1.
Figure 6B:
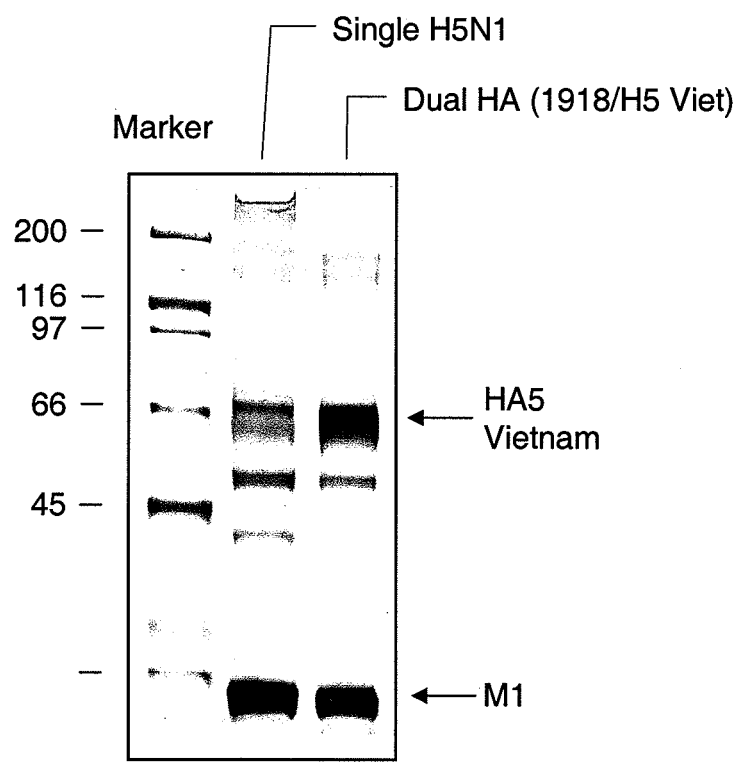

Western blot analysis of purified polyvalent VLPs with a mouse monoclonal antibody against the 1918 HA (generously provided by Dr. Palese, Mount Sinai School of Medicine) and a rabbit polyclonal antibody against influenza virus A/Vietnam/1023/04 (H5N1) (generously provided by Dr. Donis, Influenza Branch, CDC) demonstrated that both molecules were present in the purified VLP preparation. (FIG. 6).

In order to determine whether the two HA molecules were incorporated onto the surface of the same particle or segregated onto the surface of different virus-like particles (VLPs), differential immuno-precipitation/Western blot analysis was carried out. In this experiment, purified VLPs were incubated first with either a mouse anti-1918-HA Mabs or a rabbit anti-avian influenza HA5 (raised against a synthetic peptide) and then precipitated with protein G conjugated to beads. Subsequently, the individually precipitated VLPs were SDS-PAGE separated and Western blot analyzed.

Figure 10:
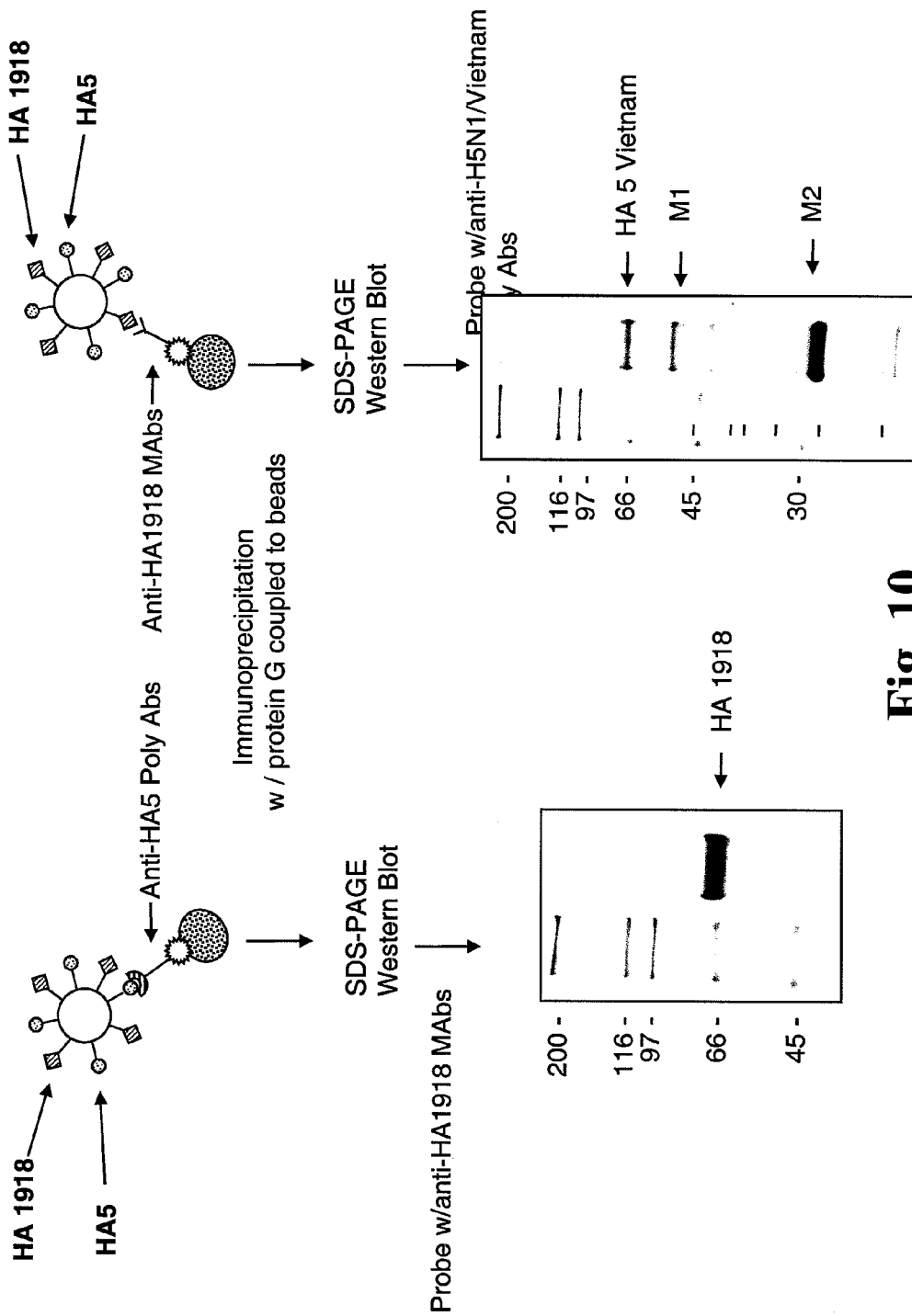
FIG. 10 is a schematic depicting Western blot/Immunoprecipitation analysis demonstrating that two different HA molecules (HA5 and HA1918) are expressed on the same surface of the same polyvalent VLP. See, Example, 1. Both blots show markers in the left lane and dual HA VLP in the right lane. The blots show that the VLPs contain both HA 1918 (left blot), HA5 Vietnam (right blot) on their surface, in addition to M1 (right blot) and M2 (right blot) proteins.

The VLPs precipitated with the 1918-HA Mabs were probed with a rabbit polyclonal against the flu A/Viet/1023/04 (H5N1) and vice versa, the VLPs that were precipitated with the rabbit anti-HA5 (synthetic peptide) were probed with the 1918-HA Mabs. These experiments showed that the VLP precipitated with the HA1918 Mabs did contain the HA5 molecules on their surfaces as demonstrated by positive Western blot when probed with fluA/Viet/1023/04 (H5N1) (FIG. 10).

Similarly, VLPs precipitated with anti-fluA/Viet/1023/04 (H5N1) and probed on Western blots with the 1918-HA Mabs were also positive for the 1918 HA demonstrating again that both HA molecules were present on the surfaces of the same particle. The Western blot probed with the fluA/Viet/1023/05 (H5N1) rabbit polyclonal antibody showed, in addition to HA5, the other VLP structural components, flu proteins M1 and M2. (FIG. 10).

Electron Microscopy

Figure 7A:
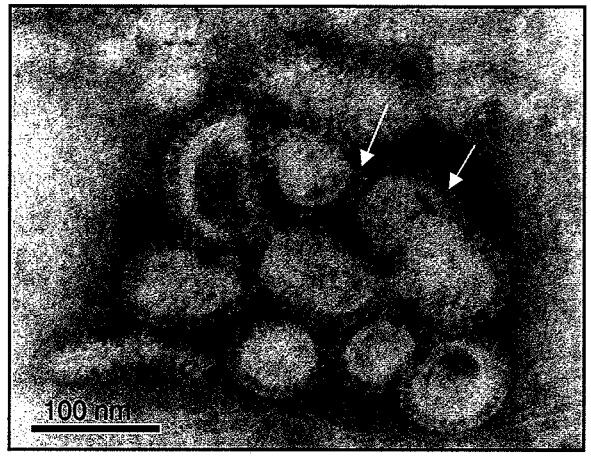
FIG. 7A shows negative straining of polyvalent VLPs and depicts polymorphic influenza-virus like structures. Arrows point to HA spikes.

To observe the morphology and confirm the surface antigenic composition of the polyvalent VLPs, we examined purified polyvalent VLPs by negative staining and dual immunogold-labeling electron microscopy. The negative staining examination showed that the particles maintained an influenza virus-like morphology with typical surface projections radiating from the entire surface. (FIG. 7A)

Figure 7B:
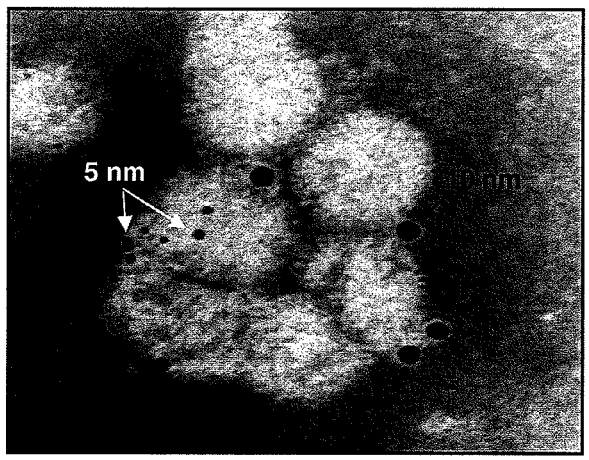
FIG. 7B show results of dual immuno-gold labeling of VLPs with anti-1918 HA (10 nm gold particles) and anti-HA5 (5 nm gold particles) antibodies.

Furthermore, purified polyvalent VLPs were also examined by negative staining after dual immuno-gold labeling. For these experiments, purified polyvalent VLPs were first incubated with a mixture of anti-1819 HA (mouse Mabs) and anti-HA5 (rabbit anti-avian influenza HA5-peptide) antibodies and subsequently incubated with a mixture of anti-mouse (conjugate to 10 nm gold beads) and anti-rabbit (conjugated to 5 nm gold beads). Immuno-gold labeled particles were then examined by negative staining EM (FIG. 7B).

Hemagglutination/ELISA Assays

Studies were also performed to determine their activity in hemagglutination assays, which can be abrogated by the addition of specific antibody directed against either of the two HA molecules present on the surface of the particles.

In the first set of experiments, purified polyvalent influenza VLP vaccine was tested in an ELISA assay. In this study, purified polyvalent influenza virus-like particles were used as antigen to coat ELISA plates. Subsequently, different rows of the VLP coated plates were incubated in triplicate with two-fold serial dilutions of three different specific antibodies as follows: a) Anti-1918 HA mouse Mab (kindly provided by Dr.

Peter Palese, Mount Sinai School of Medicine), b) Anti-HA5 rabbit polyclonal antibody (US Biological,), C) Anti-HA3 mouse Mab (Roche Laboratory). Each group had a PBS row without primary antibody as a control. After 3 washes the following horseradish peroxidase (HRP) conjugated secondary antibodies were added to the following rows: The A and C rows (anti-1918 HA and anti-HA3 mouse Mab respectively) received HRP conjugated goat anti-mouse and the row B (anti-HA3 rabbit polyclonal) HRP conjugated goat anti-rabbit, both from Bio-Rad Laboratories. The plates were then developed using one step Ultra TMB substrate (Pierce) and read on a plate reader at 450 nm absorbance.

Figure 8:
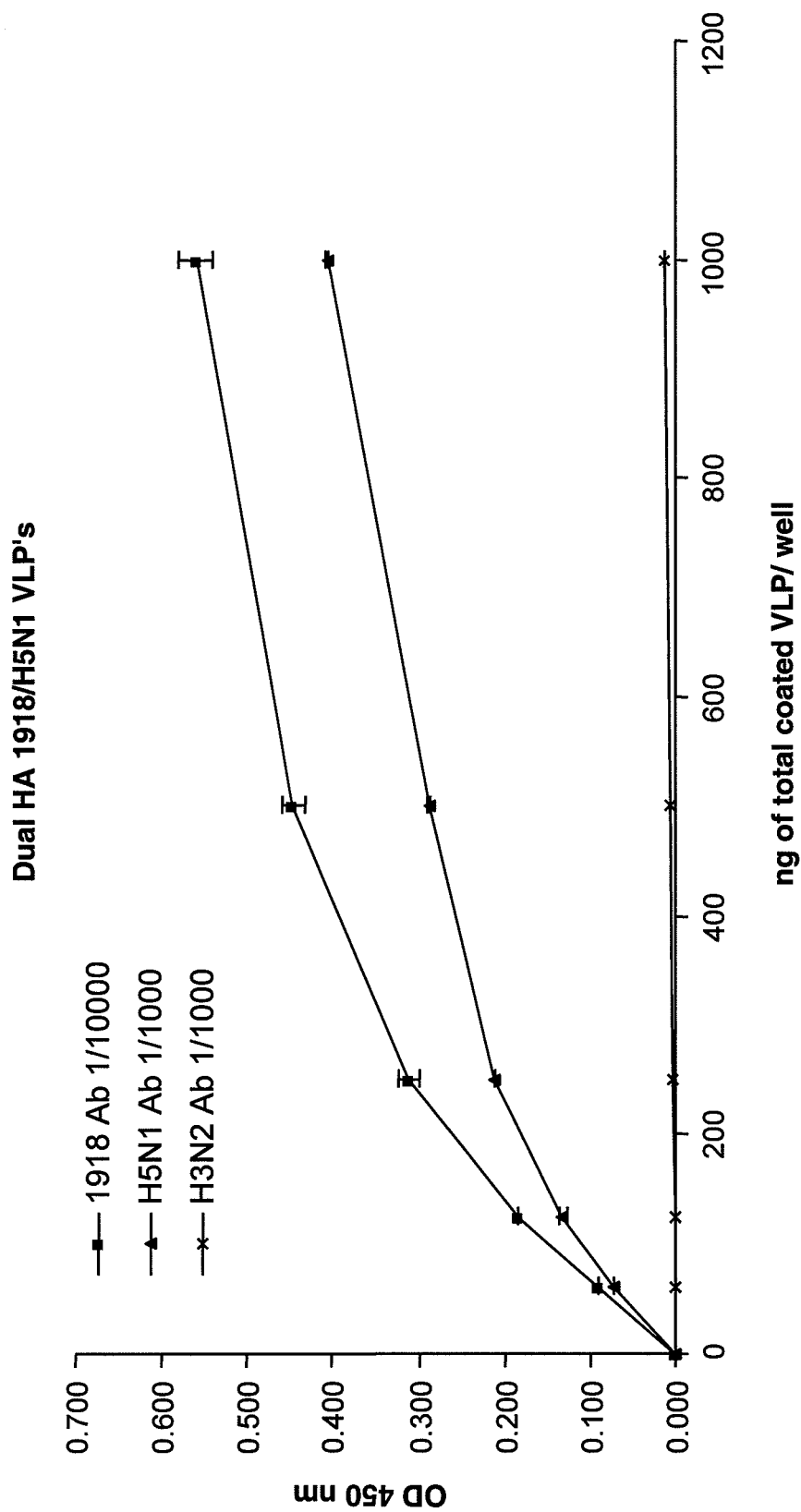
FIG. 8 is a graph depicting ELISA assay results. When an anti-H3N2 antibody was used in the ELISA, no signal was detected.

This study showed that the anti-1918 HA and anti-H5 antibodies recognized specific antigens on the polyvalent VLP vaccine which was used as antigen to coat the ELISA plate (FIG. 8). On the other hand, the anti-HA3 antibody was unable to react with the polyvalent vaccine, as expected, because the HA3 molecule was not included in the polyvalent VLP vaccine (FIG. 8). Thus, the two antigenically distinct HA molecules are independently detected by both of two specific antibodies anti-1918 HA and anti-HA5 whereas a non-specific anti-HA3 did not show binding on the polyvalent VLP vaccine (FIG. 8).

In order to evaluate the ability of the polyvalent VLP vaccine to agglutinate red blood cells (RBC), a typical attribute of the influenza viruses, we performed hemagglutination assays with purified polyvalent VLP vaccine and turkey red blood cells. This test showed that the polyvalent VLPs were able to agglutinate red blood cells (first row, HA assay-no Ab in the hemagglutination inhibition test presented in FIG. 9)

Given the fact the polyvalent VLPs agglutinate RBC's, we postulated that antibody against either of the two HA molecules incorporated on the surface of the VLPs should have an inhibitory effect on the hemagglutination activity of the polyvalent VLP vaccine. To test this assumption, we used the anti-1918 HA Mabs (described above) and a rabbit polyclonal anti-HA5 Vietnam (kindly provided by Dr. Ruben Donis, CDC). Prior to the assay, each antibody was treated with the receptor destroying enzyme (RDE II Seiken, Accurate Chemicals, Westbury, N.Y.) and absorbed with turkey RBC to remove nonspecific agglutinins and inhibitors. Treated antibodies (1:5 final dilution after treatment) were two-fold serially diluted in a 96-well V-shaped bottom plate and subsequently incubated with 4 HA units of polyvalent VLP. Following polyvalent VLP-antibody incubation, a 0.5% solution of turkey RBCs was added to the wells. Additional incubation was allowed and inhibition of hemagglutination was observed when a sufficient amount of antibody, specific to the viral or VLP antigens, blocked VLP agglutination of the RBC, which is visualized by a RBC button at the base of the well (FIG. 9).

This study showed not only that polyvalent VLPs are able to agglutinate turkey RBCs but also that a specific antibody against either of the two HA molecules was able to partially inhibit the agglutinating activity of the particles. Furthermore, when the hemagglutination inhibition test was carried out with a mixture of the two antibodies (anti-1918 HA plus anti-H5) the agglutination activity was completely abrogated (FIG. 9, complete inhibition). Non-specific antibodies, on the other hand, did not abrogate the hemagglutination activity of the polyvalent VLP vaccine.

Figure 9:
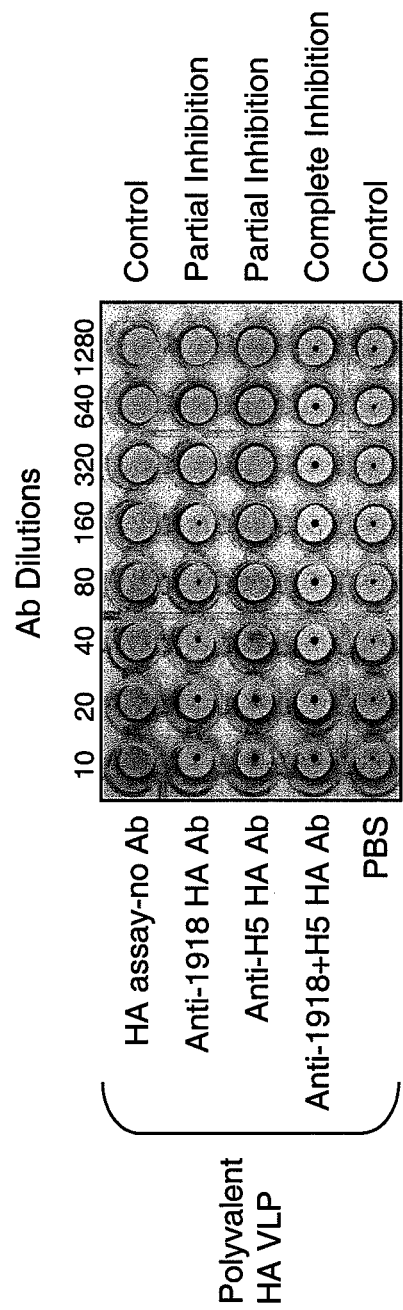
FIG. 9 depicts a hemagglutination inhibition (HAI) assay of polyvalent VLPs incubated with both anti-1918 HA and anti-H5 HA Vietnam antibodies.

These experiments therefore, have clearly shown that the HA molecules on the surface of the VLPs are functional in the agglutination of RBC which can be partially abolished by either one of the specific antibodies (anti-1918 HA or Anti-HA5) or completely eliminated by a mixture of the two (FIG. 9).

Thus, polyvalent influenza virus-like particles (VLPs) bearing on their surfaces two antigenically distinct HA molecules were prepared.

Example 2

Modification of Influenza M1 Protein-Encoding Sequences

A. Deletion and/or Mutation of Nuclear Localization Signal

The polynucleotide sequence encoding an M1 protein from a selected influenza virus strain A/PR/8/34 is isolated. One or more of all the nuclear localization signal (positions 101-105, relative to wild-type A/PR/8/34, having the amino acid sequence RKLKR (SEQ ID NO: 1) are deleted or modified.
B. Specific Mutations that Determine Spherical Sub-Viral Structure Formation The morphology of wild type virus particles varies from an elongated rod-shape to structures that are more or less spherical. Specific determinants on the sequence of the matrix proteins appear to influence this morphological trait.

To maximize the assembly and release of homogeneous spherical sub-viral structure vaccine, specific amino acids changes are introduced on the primary sequence of the matrix proteins, for example, at amino acid positions 41, 95, 98, 167, 204, 205 and/or 218 (FIG. 2).
Modification of Residues Involved in Monomers Contact and Sub-Viral Structure Yield Viral matrix protein associates with the plasma membrane and establishes contact with other protein monomers forming an oligomerized scaffold, which together with the other components drives the release of the sub-viral structure from the cell of synthesis and assembly. Site specific changes as shown in Table 1 in the primary sequence of the matrix protein enhances protein-protein and protein membrane interactions promotes higher specificity and better yield of the polyvalent sub-viral structure vaccine.
Modification of One or More Sequence Specific Motifs (L-Domains)

Sequence specific motifs (L-domains) (FIG. 2) are critical in recruiting host proteins which are necessary for the budding and pinching off of the sub-viral structure from the cell membrane. Insertion of one or more L-domains at alternative locations within the sequence of the matrix proteins significantly enhances bud formation and release of sub-viral structures from the surface of producing cells.

The DNA sequence coding for this modified matrix 1 (M1) protein is used for the production of each polyvalent vaccine utilizing this design.

Example 3

Modifications to Influenza Matrix Protein 2 (M2)

M2 protein is a trans-membrane protein that as a tetramer forms an ion channel at the surface of the virus particle. The amount of M2 protein incorporated into the wild type virus represents approximately 2% of the amount of M1 proteins.

Figure 3:
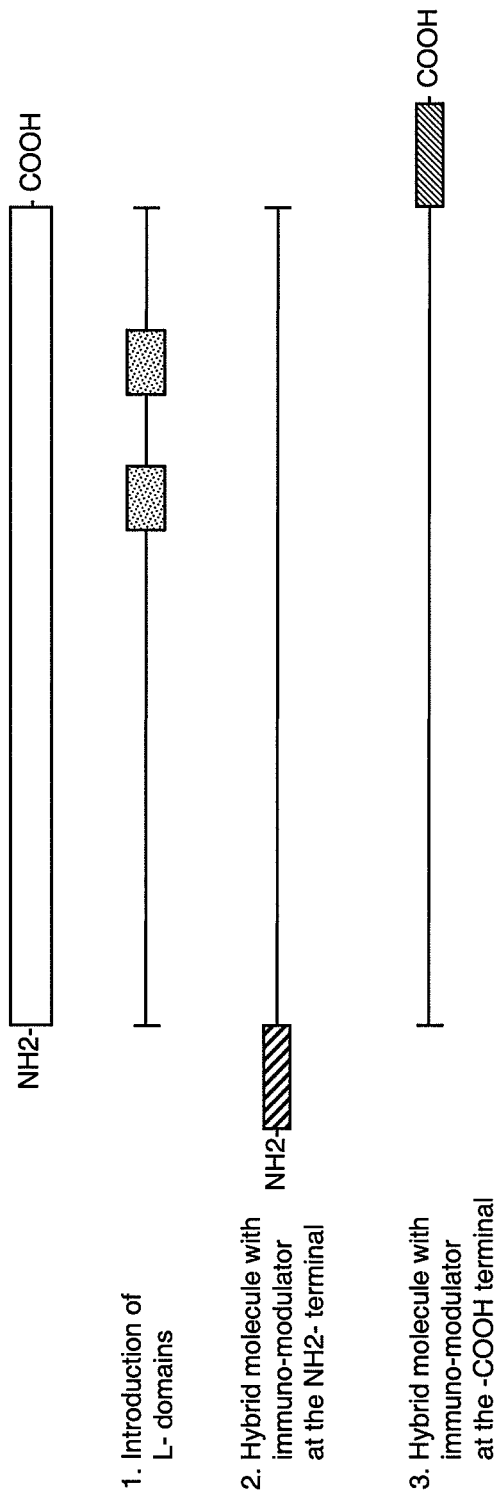
FIG. 3 is a schematic depicting exemplary amino acid sequence modifications to matrix protein 2 (M2). These modifications may enhance incorporation and/or potency of polyvalent influenza VLPs as described herein.
Figure 4:
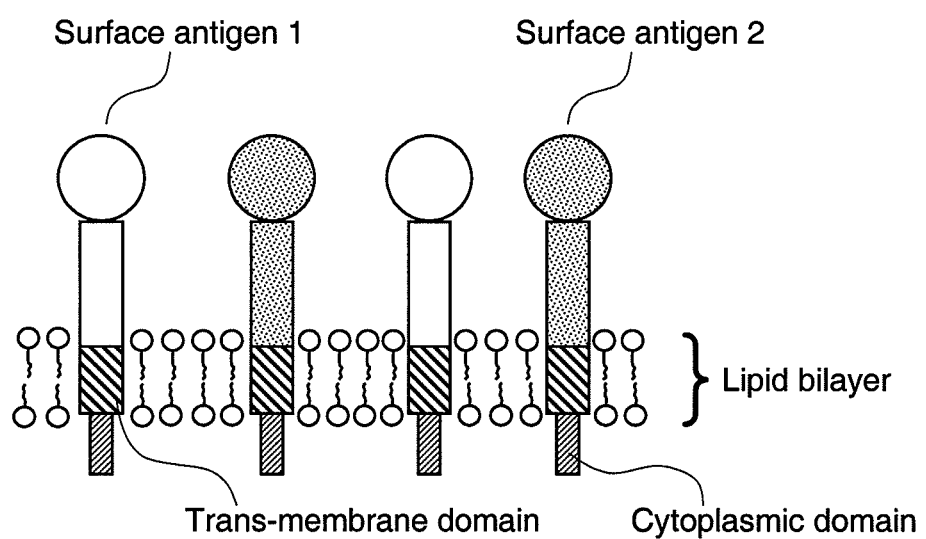
FIG. 4 is a schematic diagram showing an exemplary polyvalent VLP as described herein in which the transmembrane and/or cytoplasmic tail domains of the surface antigens (e.g., glycoproteins HA and/or NA) are replaced with homologous domains from other influenza.

Modifications to M2 are made as shown in FIG. 3, for example to the L-domains; and/or inclusion of sequences encoding immunomodulatory polypeptides at the amino and/or carboxy terminals. Such modifications increase incorporation into the sub-viral structure vaccine and/or modulate the type or potency of immune response elicited by the sub-viral structure vaccine by engineering hybrid M2 proteins that carry attached to its extra-cellular domain immune receptors, immune-modulators and/or adjuvant molecules.

Example 4

Sequences Encoding Chimeric HA and NA Polypeptides

As described above in Example 1, to aid in incorporation of the desired antigens onto the surface of the sub-viral structure, the sequences encoding the trans-membrane and cytoplasmic tail sequences of the selected HA- and/or NA-encoding sequences are replaced with the corresponding HA and/or NA of influenza virus strain A/PR/8/34 virus. See, also, FIG. 4. This allows for better interaction with the plasma membrane as well as with the underlying matrix proteins. In addition, identical trans-membrane and cytoplasmic domains in both surface molecules will aid in directing a similar level of incorporation of components into the sub-viral structure vaccine.

Example 5

Polyvalent Influenza VLPs

The sequences described above are introduced into one or more expression vectors (e.g., baculovirus, plasmid) and introduced into suitable host cells under conditions where polyvalent VLPs are formed. VLP formation is confirmed by Western blot analysis, neuraminidase assay and/or standard hemagglutination assays. See, also, U.S. Patent Publication No. 20050186621.

Example 5

In Vivo Vaccination with Polyvalent Influenza VLPs

The immunogenicity and protective efficacy of polyvalent VLP vaccines are tested in BALB/C mice (Charles River Laboratories, Wilmington, Mass.). Mice are immunized intranasally or intramuscularly with single or multiple doses of polyvalent VLPs as described herein.

What is claimed is:

1. A noninfectious polyvalent influenza VLP comprising an influenza M1 protein, an influenza M2 protein and two or more influenza HA glycoproteins, wherein
   (i) the polyvalent VLP comprises two or more antigenic influenza hemagglutinin (HA) glycoproteins from two or more different influenza strains;
   (ii) the two or more HA glycoproteins are displayed on the surface of the VLP;
   (iii) a portion of one or more of the HA glycoproteins is replaced with a homologous region of a HA from a different influenza strain of the same type; and
   (iv) the influenza M2 protein comprises an amino acid modification as compared to a wild-type M2 protein, wherein the amino acid modification is selected from the group consisting of addition or substitution of an influenza M protein L-domain to the M2 protein, addition of an immunomodulatory sequence to the N-terminus of the M2 protein, addition of an immunomodulatory sequence to the C-terminus of the M2 protein and combinations thereof.

2. The noninfectious polyvalent influenza VLP of claim 1, further comprising an influenza nucleoprotein (NP).

3. The noninfectious polyvalent influenza VLP of claim 1, further comprising less than all of the proteins of an influenza polymerase complex.

4. The noninfectious polyvalent influenza VLP of claim 1, wherein the VLP further comprises one or more NA glycoproteins.

5. The noninfectious polyvalent influenza VLP of claim 1, wherein the M1 protein comprises a nuclear localization signal and further wherein the nuclear localization signal (NLS) is modified by deletion, insertion or substitution of one or more residues.

6. The noninfectious polyvalent influenza VLP of claim 1, wherein one or more influenza M protein L-domains are introduced into the M2 protein.

7. The noninfectious polyvalent influenza VLP of claim 1, wherein the transmembrane domain of the HA glycoprotein of (iii) is replaced.

8. The noninfectious polyvalent influenza VLP of claim 1, wherein the cytoplasmic tail region of the HA glycoprotein of (iii) is replaced.

9. An isolated host cell comprising a noninfectious polyvalent influenza VLP according to claim 1.

10. A method of producing the noninfectious polyvalent influenza VLP according to claim 1, the method comprising the steps of:

expressing one or more polynucleotides encoding the M1 and M2 and at least two influenza HA glycoproteins of the VLP in a suitable isolated host cell under conditions such that the VLPs assemble in the host cell;

wherein the influenza M2 protein comprises an amino acid modification as compared to a wild-type M2 protein, wherein the amino acid modification is selected from the group consisting of addition or substitution of an influenza M protein L-domain to the M2 protein, addition of an immunomodulatory sequence to the N-terminus of the M2 protein, addition of an immunomodulatory sequence to the C-terminus of the M2 protein and combinations thereof;

wherein a portion of one or more of the HA glycoproteins is replaced with a homologous region of a HA from a different influenza strain of the same type; and isolating the assembled VLPs from the host cell.

11. The method of claim 10, wherein the isolated host cell is selected from the group consisting of a mammalian cell, an insect cell, a yeast cell, a plant cell and a fungal cell.

12. The method of claim 10, wherein the one or more polynucleotides are expressed from an expression vector.

13. The method of claim 12, wherein the polynucleotides are operably linked to control elements compatible with expression in the selected host cell.

14. The method of claim 12, wherein the expression vector is selected from the group consisting of a plasmid, a viral vector, a baculovirus vector and a non-viral vector.

15. The method of claim 10, wherein one or more of the polynucleotides are stably integrated into the host cell.

16. A method of generating an immune response in a subject to two or more influenza viruses, the method comprising the step of administering an effective amount of a composition comprising the noninfectious polyvalent influenza VLP according to claim 1 to the subject.

17. The method of claim 16, wherein the composition is administered intranasally.

18. The method of claim 16, wherein the composition is administered in a multiple dose schedule.

19. An immunogenic composition comprising the noninfectious polyvalent influenza VLP of claim 1 and a pharmaceutically acceptable excipient.

20. The immunogenic composition of claim 19, further comprising an adjuvant.

* * * * *